US006402742B1

(12) United States Patent
Blewett et al.

(10) Patent No.: US 6,402,742 B1
(45) Date of Patent: Jun. 11, 2002

(54) CONTROLLER FOR THERMAL TREATMENT OF TISSUE

(75) Inventors: Jeffrey J. Blewett, Plantsville; Christopher J. Maurer, Newtown, both of CT (US); Corbett W. Stone, San Diego, CA (US)

(73) Assignee: United States Surgical Corporation

( * ) Notice: Subject to any disclaimer, the term of this patent is extended or adjusted under 35 U.S.C. 154(b) by 0 days.

(21) Appl. No.: 09/500,326

(22) Filed: Feb. 8, 2000

Related U.S. Application Data

(63) Continuation of application No. 09/095,239, filed on Jun. 10, 1998, now abandoned, which is a continuation of application No. 08/948,990, filed on Oct. 10, 1997, now abandoned.
(60) Provisional application No. 60/043,658, filed on Apr. 11, 1997.

(51) Int. Cl.[7] ............................ A61B 18/04; A61B 18/18
(52) U.S. Cl. ............................ 606/34; 606/37; 607/101
(58) Field of Search ........................ 606/34, 37, 38–42, 606/45, 48, 49; 607/96, 98, 99, 101, 102, 115, 116, 154

(56) References Cited

U.S. PATENT DOCUMENTS

| 5,334,193 A | 8/1994 | Nardella |
| 5,413,588 A | 5/1995 | Rudie et al. ................ 607/101 |
| 5,458,597 A | 10/1995 | Edwards et al. |
| 5,472,441 A | 12/1995 | Edwards et al. |
| 5,496,271 A | 3/1996 | Burton et al. ................ 604/54 |
| 5,496,311 A | 3/1996 | Abele et al. ................ 606/28 |
| 5,507,743 A | 4/1996 | Edwards et al. |
| 5,531,676 A | 7/1996 | Edwards et al. ............... 604/22 |
| 5,540,655 A | 7/1996 | Edwards et al. |
| 5,542,916 A | 8/1996 | Hirsch et al. |
| 5,599,346 A | 2/1997 | Edwards et al. |
| 5,762,066 A | * 6/1998 | Law et al. |
| 5,800,484 A | 9/1998 | Gough et al. ................ 607/104 |
| 5,807,395 A | 9/1998 | Mulier et al. ................. 606/41 |
| 5,810,804 A | 9/1998 | Gough et al. ................. 606/41 |
| 6,241,725 B1 | * 6/2001 | Cosman ...................... 606/41 |
| 6,254,598 B1 | * 7/2001 | Edwards et al. ............... 606/41 |

FOREIGN PATENT DOCUMENTS

| WO | WO 10367 | 4/1996 |
| WO | WO 34571 | 11/1996 |

* cited by examiner

Primary Examiner—Roy Gibson

(57) ABSTRACT

Disclosed is an apparatus for use in conjunction with an RF ablation electrode insertable into a patient to ablate body tissue, e.g., prostate tissue of a patient with a BPH condition. The apparatus includes an RF generator for outputting RF current through the ablation electrode and a second electrode in contact with the patient to thereby ablate body tissue in the vicinity of the ablation electrode. Temperature measuring circuitry within the apparatus is coupled to a temperature sensor in a specific body region. An input means such as a plurality of switches on the apparatus housing is provided to enable a user to input a treatment volume corresponding to a target volume of body tissue to be ablated. Delivery of RF power is automatically terminated when a treatment time corresponding to the selected treatment volume is reached. In addition, a hypertonic saline syringe is preferably housed within the controller. Saline solution is caused to flow from the syringe into the treatment region at a controlled rate both immediately prior to and during the delivery of RF power.

31 Claims, 35 Drawing Sheets

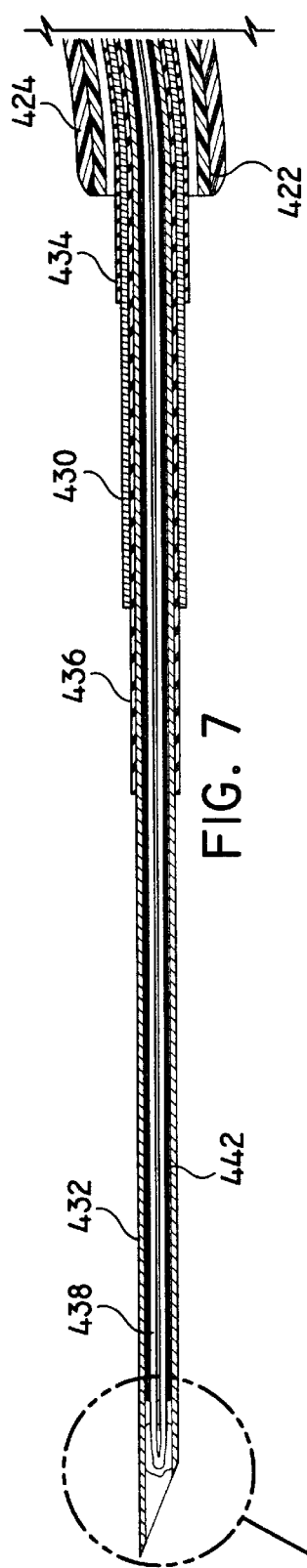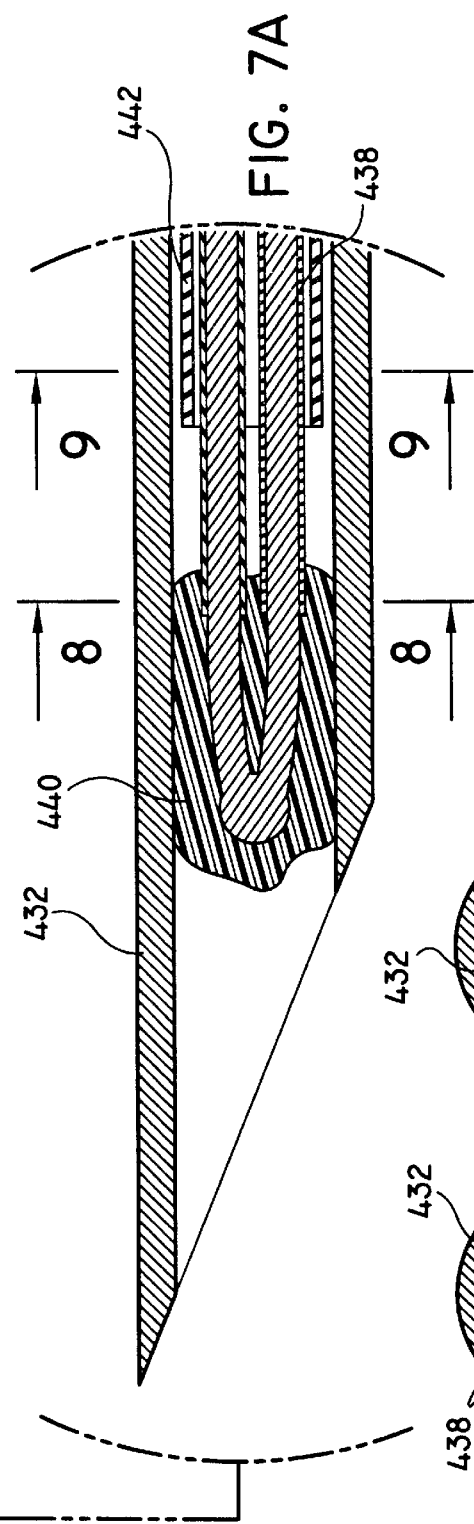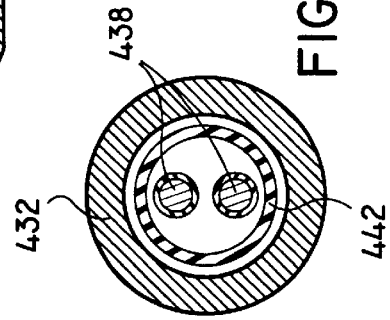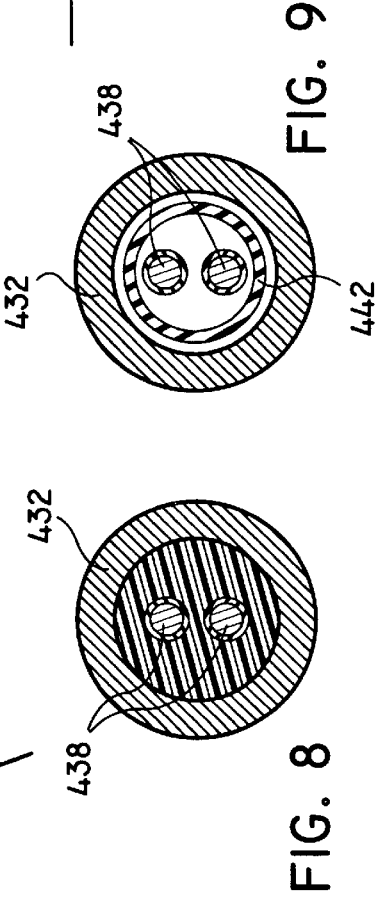

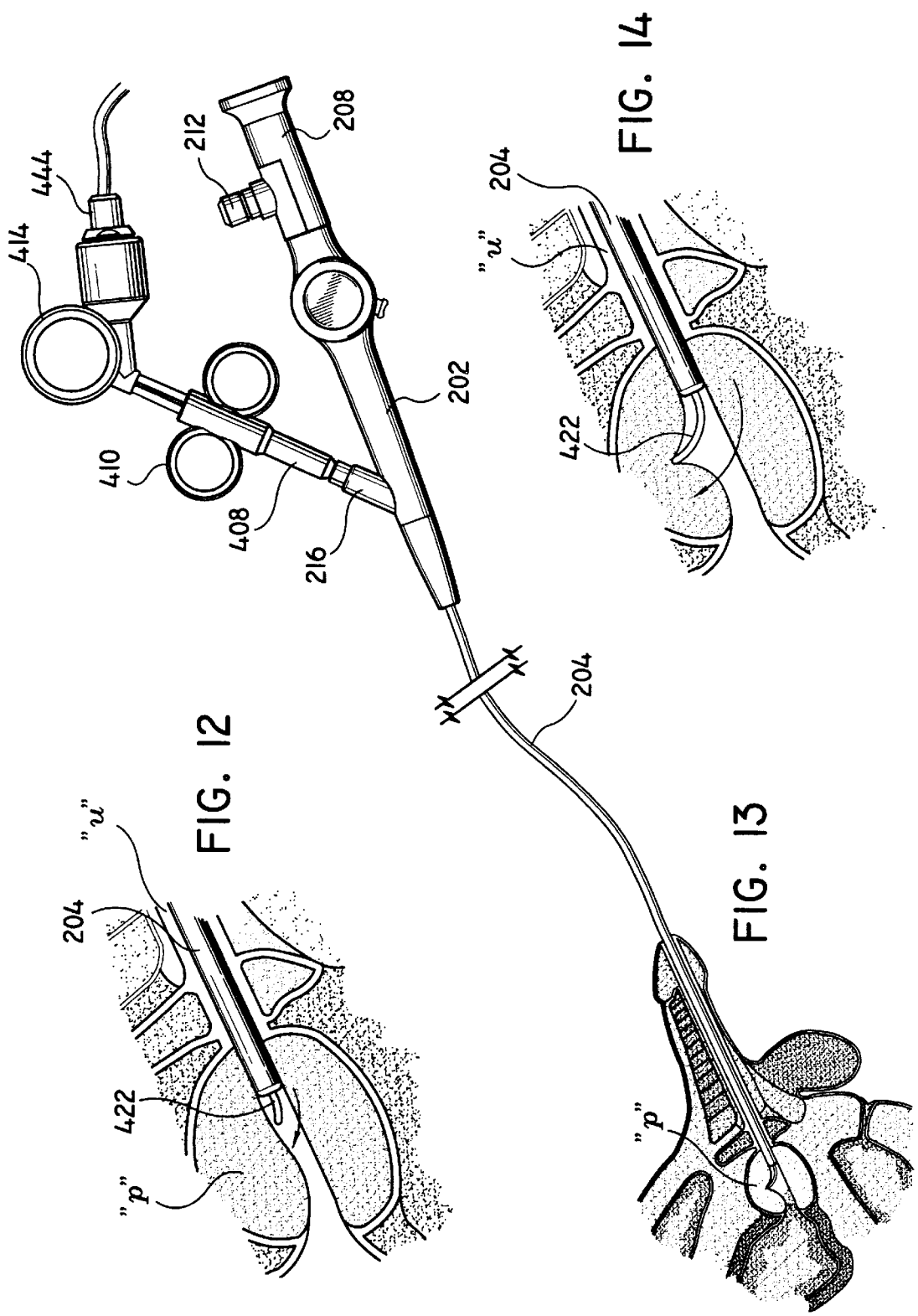

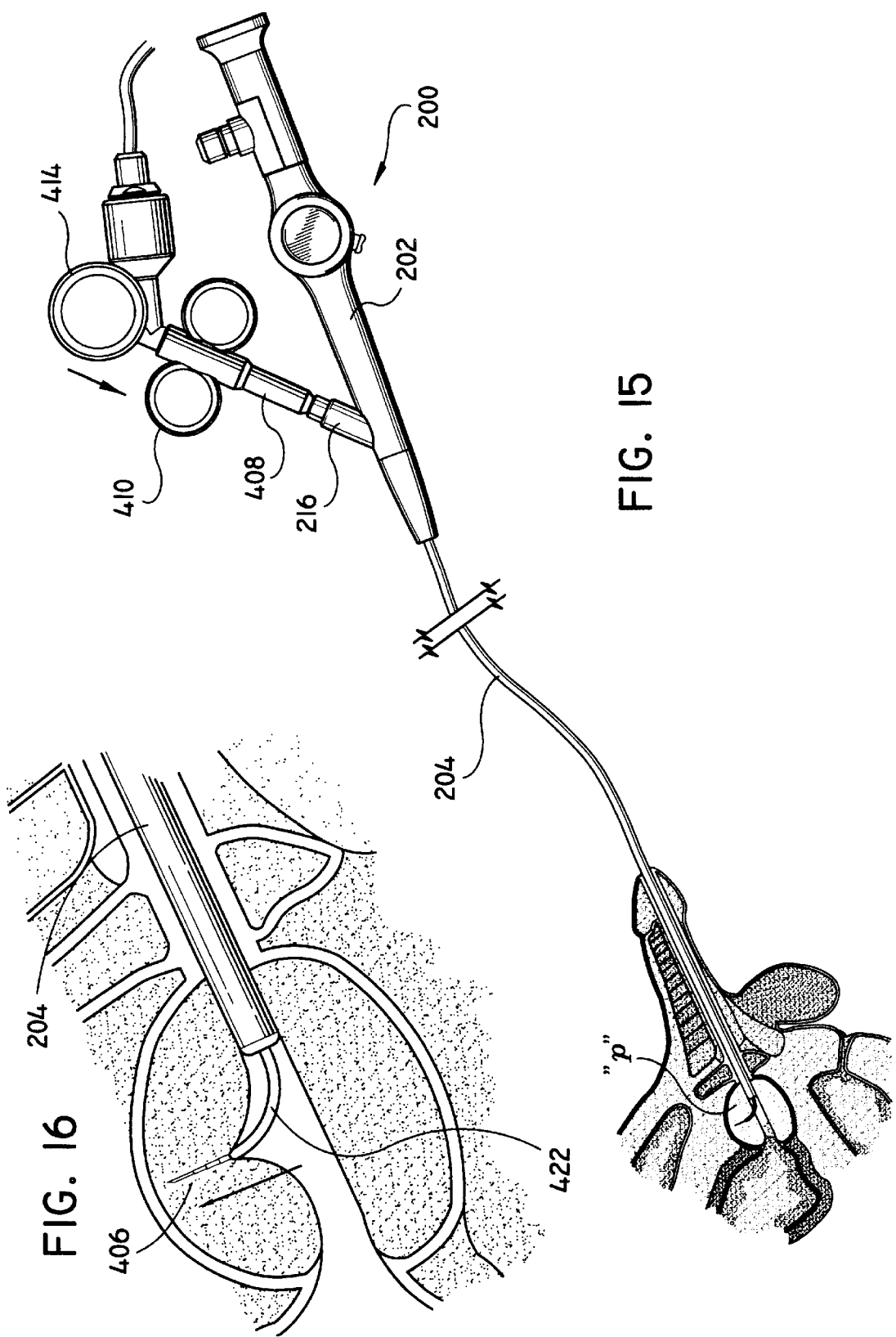

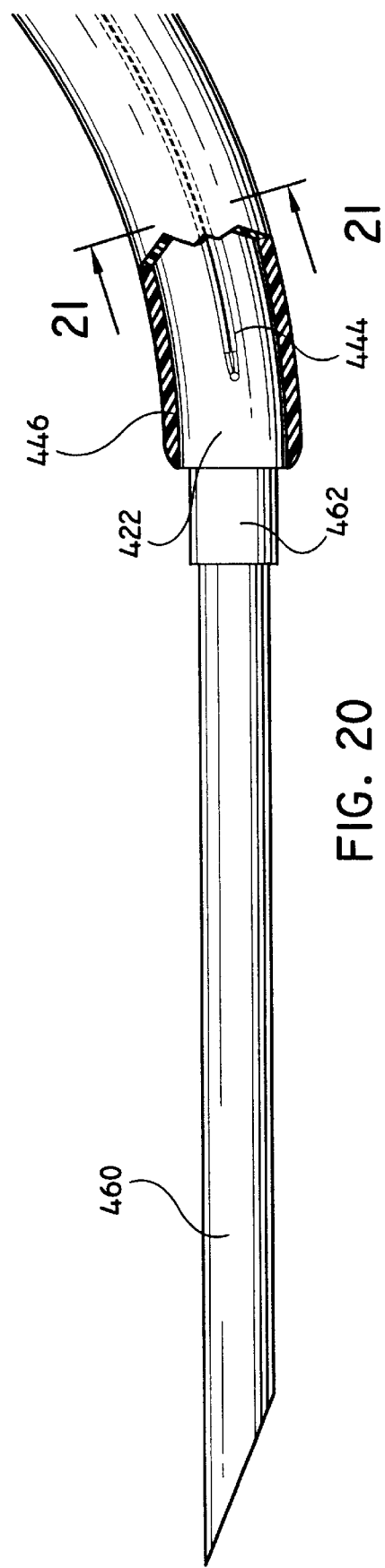
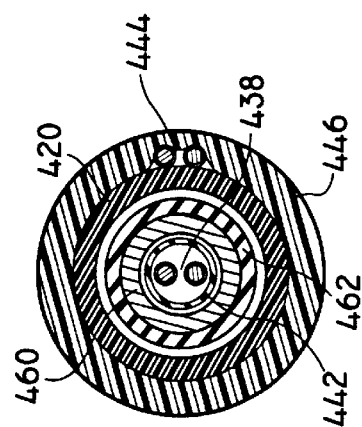
FIG. 20
FIG. 21

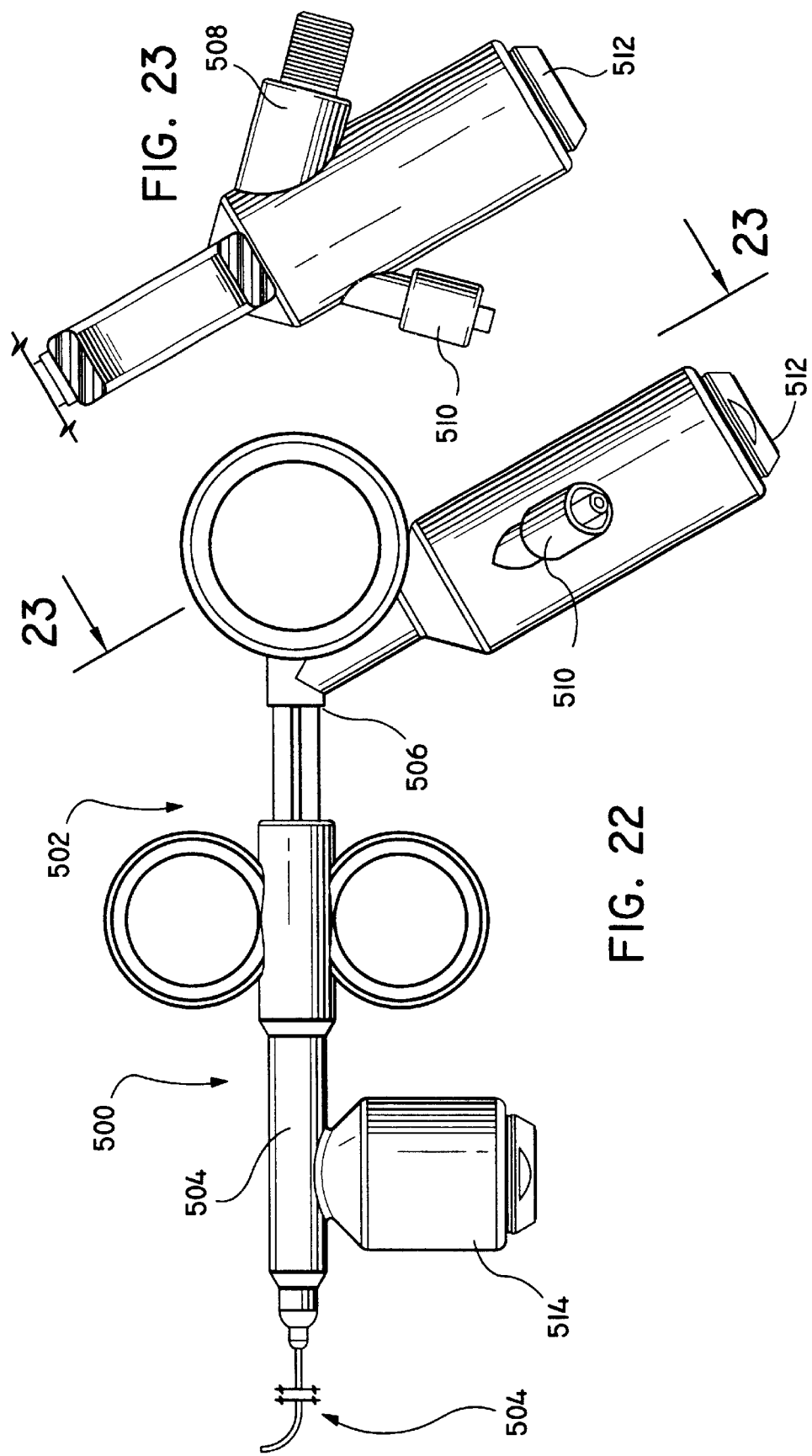

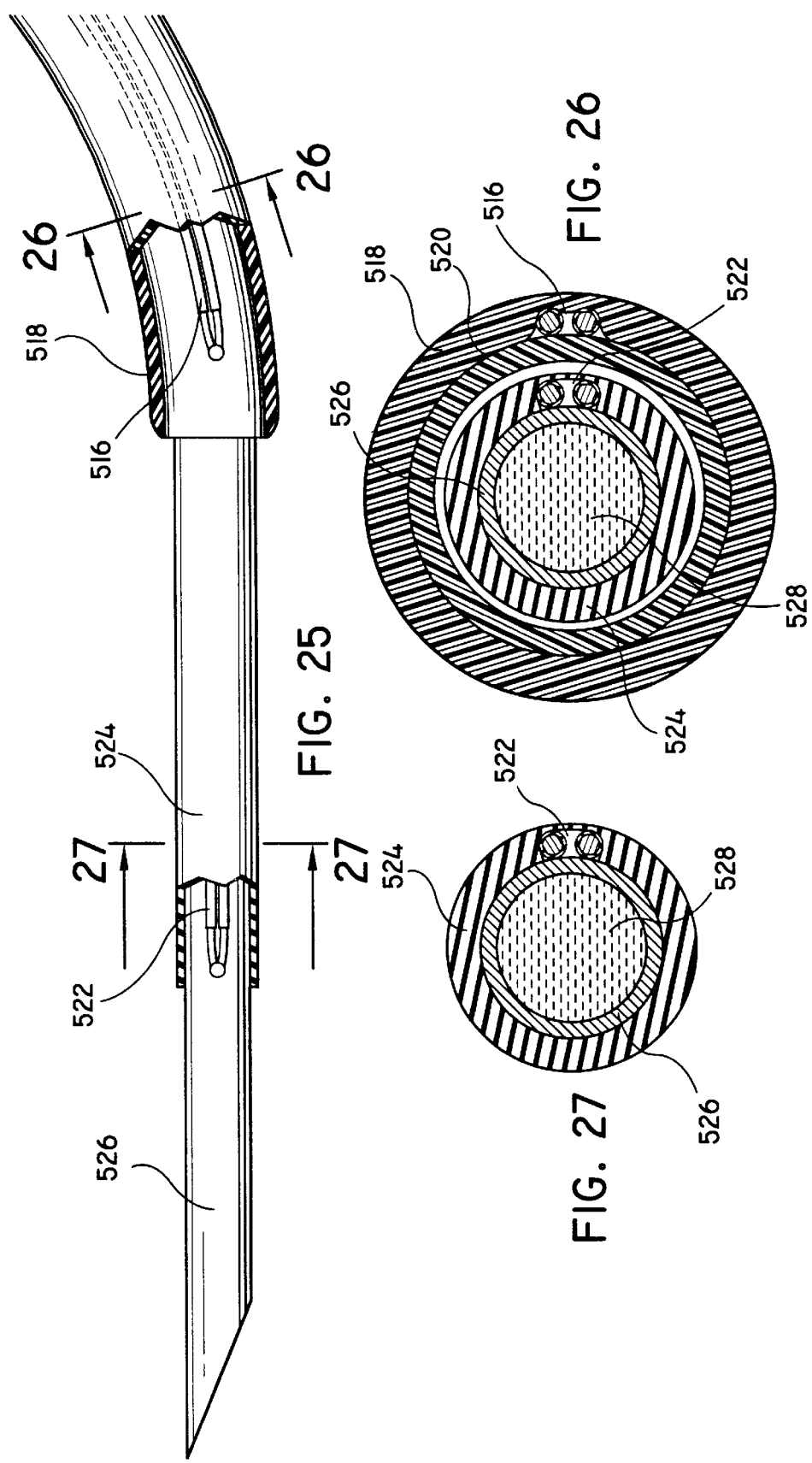

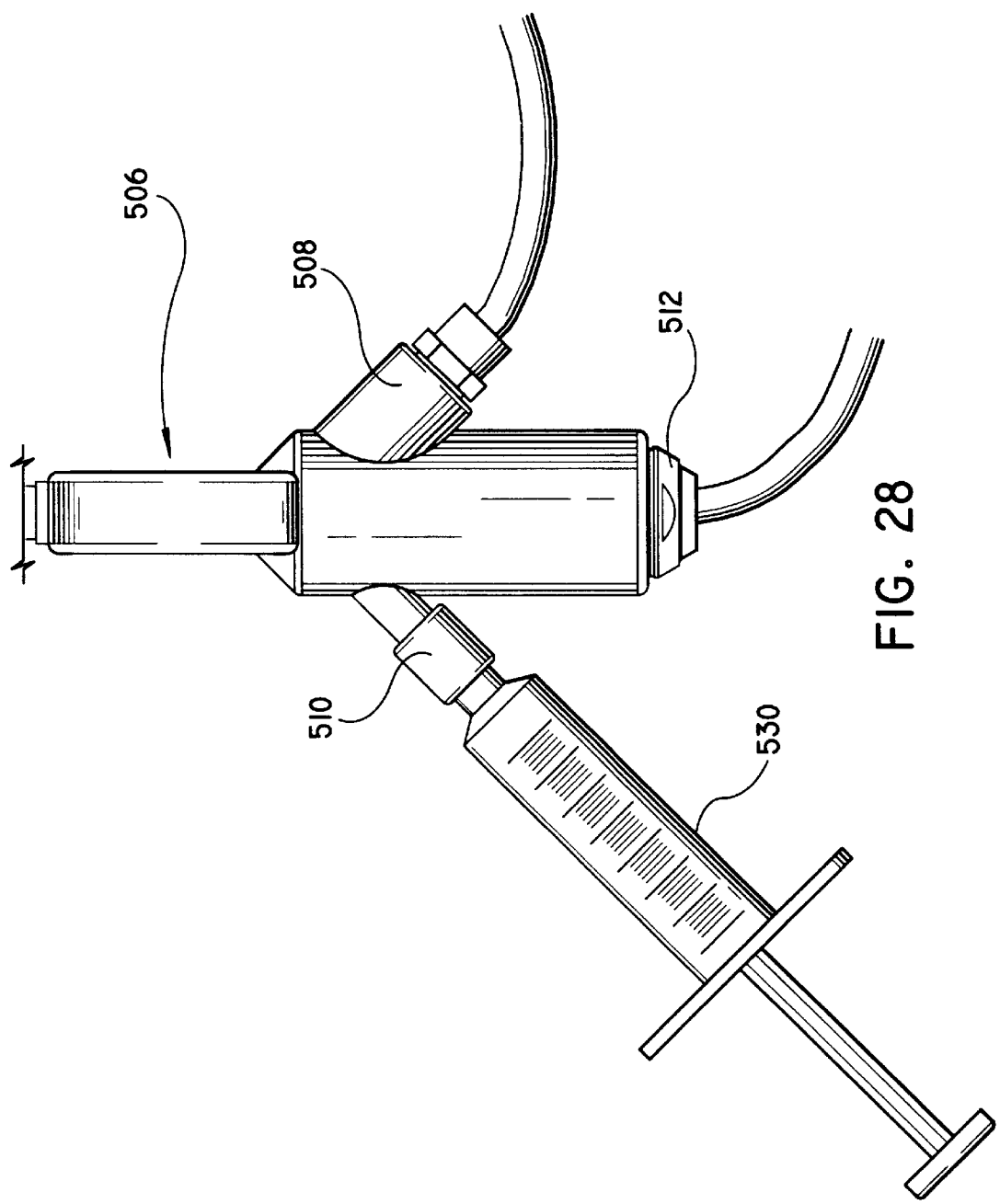

CONTROLLER FOR THERMAL TREATMENT OF TISSUE

This application is a Continuation in Part of prior application Ser. No. 09/095,239 filed on Jun. 10, 1998. Now abandoned, which is a continuation of Ser. No. 08/948,990 filed Oct. 10, 1997, abandoned.

This application claims priority from U.S. Provisional Application Ser. No. 60/043,658, entitled CONTROLLER FOR THERMAL TREATMENT OF TISSUE, filed Apr. 11, 1997, by Blewett et al., and assigned to the assignee herein.

TECHNICAL FIELD

The present disclosure relates generally to a controller for thermal treatment of tissue, and, more particularly, to a processor-based controller for Benign Prostatic Hypertrophy (BPH) treatment via transurethral diathermy.

BACKGROUND OF THE RELATED ART

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, complications in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, retrograde ejaculation, impotence, incontinence, edema and a prolonged recovery period for the patient.

A more recent form of treatment for BPH involves thermally treating prostatic tissue with radio frequency (RF) electromagnetic energy. For example, one current technique, known as transurethral needle ablation (TUNA™), involves the transurethral application of a medical instrument having a built-in RF needle electrode system. The TUNA™ instrument is inserted into the urethra and advanced to a position adjacent the prostate. Thereafter, the RF needles are advanced to penetrate the urethral wall and access the prostatic tissue. The RF system is activated whereby a RF current is transmitted through each electrode to pass through the tissue to a grounding pad thereby forming a necrotic lesion which is eventually absorbed by the body. Apparatuses and method for treating BPH via the TUNA™ technique are disclosed for example in U.S. Pat. No. 5,366,490.

The TUNA™ technique has several disadvantages which detract from its usefulness. In particular, the TUNA™ instruments are generally complex typically incorporating built-in optical systems, aspiration systems, etc. As a result, the instruments are relatively expensive to manufacture. Moreover, the TUNA™ instruments are generally enlarged by virtue of the various systems incorporated within the instrument, thus, increasing patient trauma and discomfort during use.

Commonly assigned U.S. patent application Ser. No. 08/699,091, entitled "APPARATUS FOR THERMAL TREATMENT OF TISSUE", filed Aug. 16, 1996 (hereafter, the '091 application), and commonly assigned U.S. provisional patent application No. 60/027600, filed Oct. 4, 1996, the contents of both of which are incorporated herein by reference, disclose highly effective apparatuses for the radio-frequency (RF) thermal treatment of prostatic tissue. The apparatus disclosed in the '091 application is intended for use in conjunction with a conventional endoscope such as a cystoscope and incorporates an RF system and associated mechanism that is at least partially positionable within the working channel of the scope. The apparatus, by use in conjunction with a conventional cystoscope, makes use of the existing systems, e.g., optical and illumination, of the scope, which effectively results in a less complex and less expensive RF thermal treatment device. Furthermore, the apparatus may be used in cystoscopies as small as 5 mm (or even smaller) in diameter thereby providing a less invasive system for transurethral ablation as compared to the TUNA instruments and technique.

SUMMARY OF THE DISCLOSURE

Accordingly, the present disclosure is directed to a system and controller for use in conjunction with, for example, an RF thermal treatment apparatus to facilitate operation thereof during the treatment of the BPH condition. Generally, the system includes an RF generator for outputting RF current through a first RF ablation electrode and a second electrode in contact with the patient to thereby ablate body tissue between the two electrodes. The second electrode is preferably a plate abutting the patient's skin for a monopolar treatment mode. Temperature measuring circuitry within the apparatus is coupled to a temperature sensor in a specific body region. An input means such as a plurality of switches on the controller housing is provided to enable a user to input a treatment volume corresponding to a target volume of body tissue to be ablated. Delivery of RF power is automatically terminated when a treatment time corresponding to the selected treatment volume is reached.

The controller may further include an infusion pump, coupled to a disposable syringe mounted within the apparatus, for pumping a fluid such as saline solution out of the syringe and into the body region being treated at a controlled rate. The fluid serves to provide a more uniform ablation of body tissue. The controller may further include impedance measurement circuitry to measure the impedance between the two electrodes. The therapy is automatically terminated if the impedance rises above a threshold value.

BRIEF DESCRIPTION OF THE DRAWINGS

Preferred embodiments of the present disclosure are described herein with reference to the drawings, in which like reference numerals identify similar or identical components throughout the several views, wherein:

FIG. 7 is an enlarged cross-sectional view of the distal end of the electrode assembly and deployed beyond the directional tube;

FIG. 7A is an enlarged isolated view of the distal tip of the electrode assembly with a thermocouple positioned therein for detecting the temperature at the treatment area;

FIG. 8 is a cross-sectional view taken along the lines 8—8 of FIG. 7A;

FIG. 9 is a cross-sectional view taken along the lines 9—9 of FIG. 7A;

FIG. 12 is a view illustrating insertion of a cystoscope and mounted thermal treatment apparatus within the urethral passage with the directional tube partially deployed;

FIG. 13 is a view illustrating the cystoscope and mounted apparatus inserted within the urethral passage with the directional tube fully deployed;

FIG. 14 is an enlarged view further illustrating the directional tube deployed;

FIG. 15 is a view similar to the view of FIG. 13 illustrating the electrode assembly deployed beyond the directional tube and penetrating the prostatic tissue;

FIG. 16 is an isolated view further illustrating the electrode assembly deployed within the prostatic tissue;

FIG. 20 is a side plan view of the electrode and directional tube with the directional tube partially cut-away to illustrate a second thermocouple for detecting the temperature of the tissue adjacent the treatment area;

FIG. 21 is a cross-sectional view taken along the lines 21—21 of FIG. 20;

FIG. 22 is a side plan view of another alternate embodiment of the auxiliary thermal treatment apparatus incorporating a dissipating agent for facilitating transfer of the electromagnetic energy to the treated tissue;

FIG. 23 is a view taken along the lines 23—23 of FIG. 22 depicting components of the handle of the apparatus of FIG. 22;

FIG. 25 is a side plan view of the distal end of the elongate portion with portions of the directional tube and the electrode assembly cut-away;

FIG. 26 is a cross-sectional view taken along the lines 26—26 of FIG. 25;

FIG. 27 is a cross-sectional view taken along the lines 27—27 of FIG. 25;

FIG. 28 is a plan view of the handle illustrating a syringe connected to the handle;

DETAILED DESCRIPTION OF PREFERRED EMBODIMENTS

Although the principles of the disclosure are applicable with various instruments utilized in the RF treatment of tissue, the disclosure will be fully understood from the following illustration of its application in the RF thermal treatment apparatus disclosed in commonly assigned U.S. patent application Ser. No. 08/699,091, the contents of which are incorporated herein by reference. However, it is understood that the system disclosed herein may be used with other thermal treatment instruments and in other surgical procedures such as cardiac ablation, cancer treatment, etc. The system may be used in any minimally invasive procedure where thermal treatment of tissue is desired and access to the tissue is limited.

I. Thermal Treatment Apparatus

The apparatuses to be described are particularly intended to be used in conjunction with an endoscope such as a cystoscope, fiber scope, laparoscope, urethroscope, etc. . . . to provide the scope with thermal treatment capabilities. More specifically, the apparatuses are at least partially insertable within the working channel of an endoscope, which is positioned in the body to access a targeted tissue area to thermally treat the desired tissue.

Figure 1:
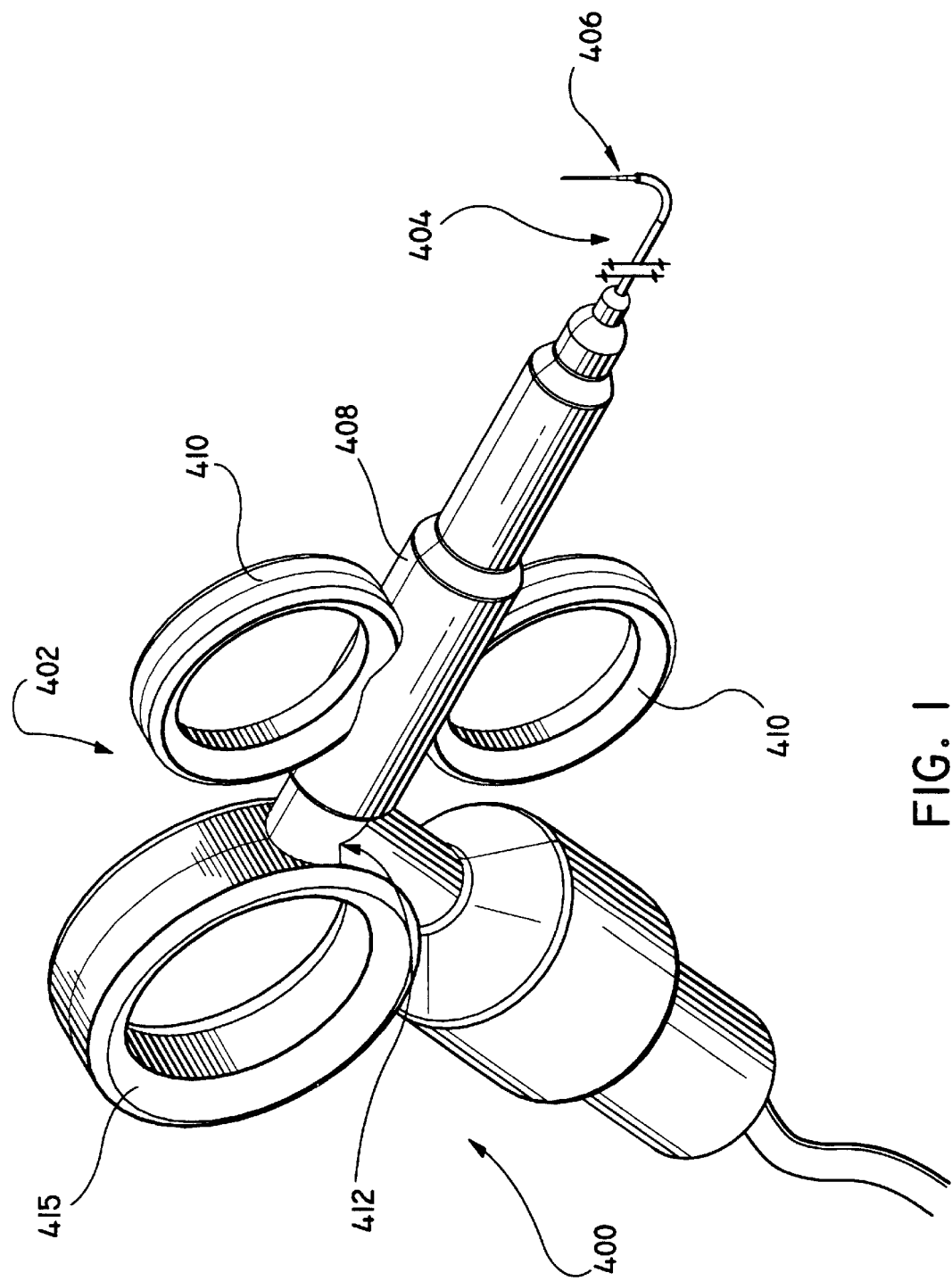
FIG. 1 is a perspective view of an embodiment of an auxiliary apparatus for thermal treatment of tissue incorporating a coaxial arranged bipolar electrode assembly.
Figure 2:
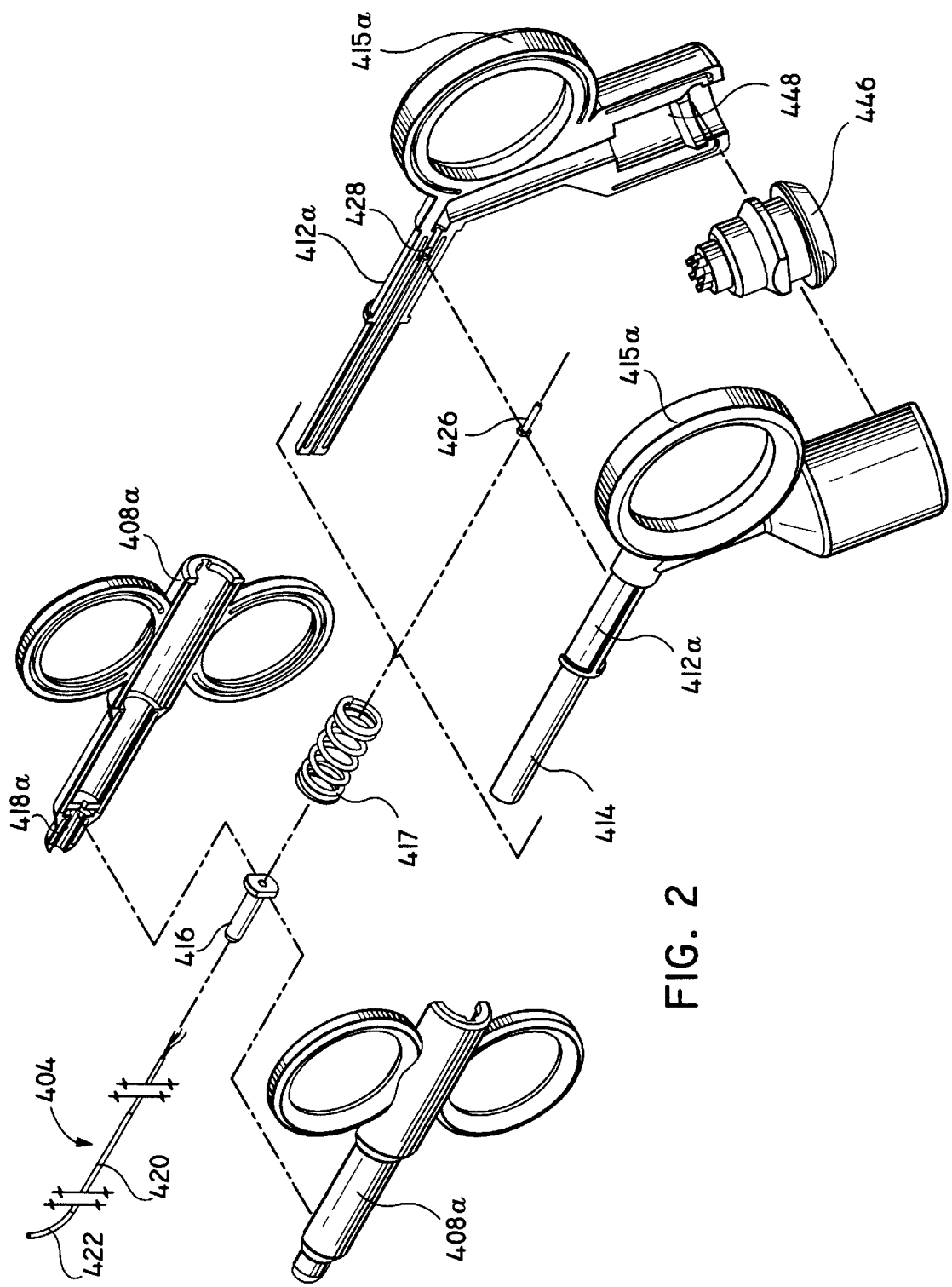
FIG. 2 is a perspective view with parts separated of the auxiliary apparatus of FIG. 1.
Figures 3, 4:
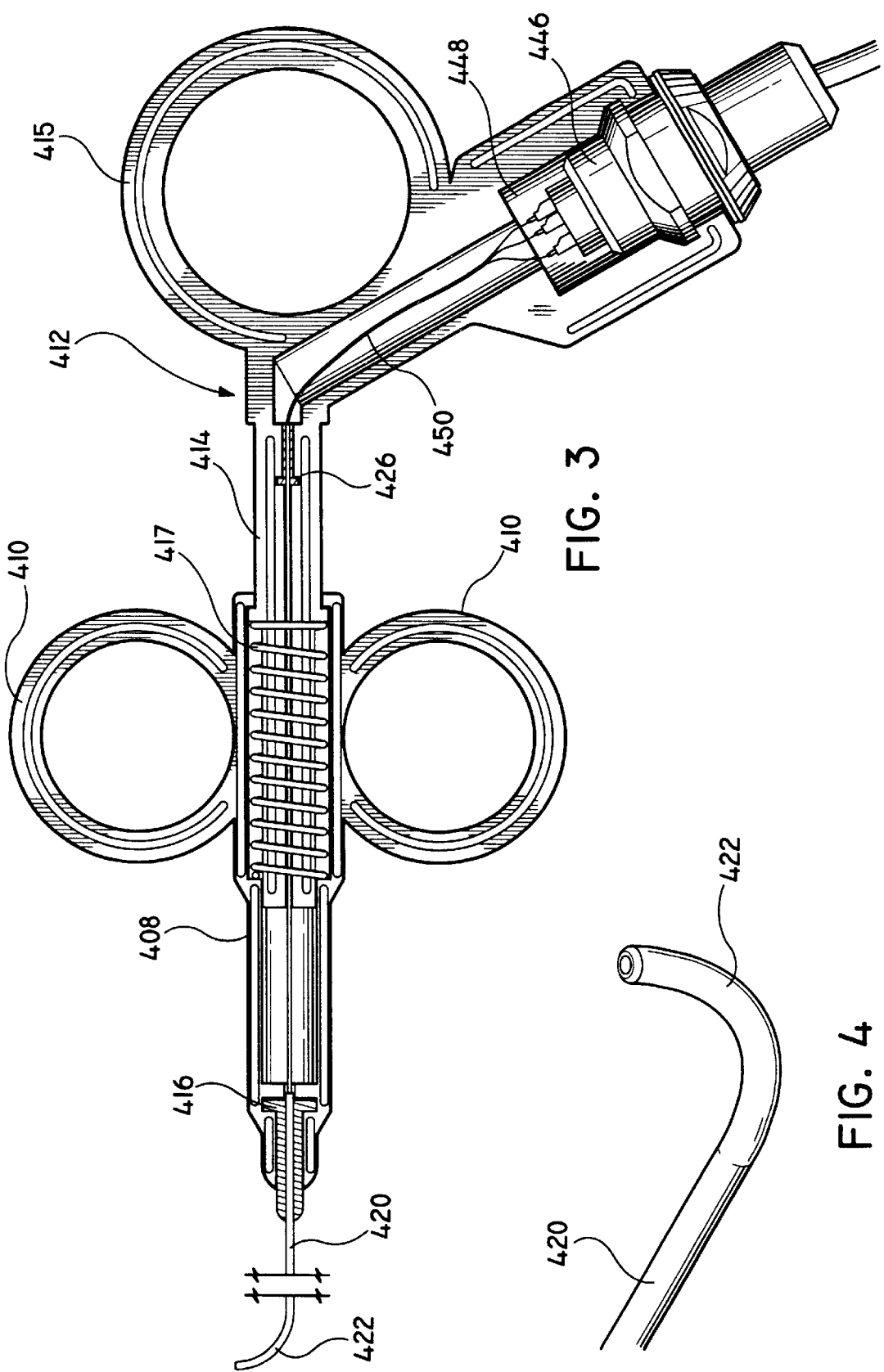
FIG. 3 is a side plan view of the apparatus with the handle in cross-section.
FIG. 4 is a perspective view of the distal end of the elongate portion of the apparatus.

Referring now to FIGS. 1–3, there is illustrated an embodiment of an auxiliary RF thermal treatment apparatus of the present disclosure, which is also one of the embodiments disclosed in the '091 application. Apparatus 400 includes housing or handle 402, elongate portion 404 connected to the handle and extending distally therefrom, and a bipolar or monopolar electrode unit 406 which extends beyond the distal end of the elongate portion 404. Handle 402 includes frame 408 defaming a generally cylindrical configuration and having diametrically opposed finger rings 410 mounted thereto. Finger rings 410 accommodate the fingers of the user to facilitate holding and manipulation of the apparatus 400. Handle 402 further includes actuating portion 412 which is mounted to frame 408.

Actuating portion 412 includes a distal inner cylindrical mounting section 414 which is received within an internal bore of frame 408 to mount the actuating portion 412 to frame 408. Mounting section 414 is dimensioned to slide within frame 408 thereby permitting relative movement between the two Components, i.e., actuating portion 412 is reciprocally moveable relative to frame 408 to operate the apparatus as will be discussed. Actuating portion 412 further includes a thumb ring structure 415 for accommodating the thumb of the user. A coil spring 417 mounted about mounting section 414 to normally bias the actuating portion 412 to a normal proximalmost position.

The components of handle 402 are preferably fabricated from a suitable rigid polymeric material or a metal such as stainless steel. The supporting components including frame 408 and actuating portion 412 preferably incorporate respective half sections 408a, 412a (FIG. 2) which are secured to each other about their peripheries with the use of adhesives, screws, etc . . .

Referring now to FIGS. 4–7, in conjunction with FIG. 2, elongate portion 404 is mounted to the distal end of frame 408 through ferrule 416 which is fixedly mounted within corresponding recesses 418 defined in frame 408 (FIG. 2). Elongate portion 404 includes outer delivery catheter 420. Outer delivery tube or catheter 420 is fabricated from a flexible material and has a shape memory portion 422 at its distal end. At its proximal end, delivery tube 420 is fixedly mounted to ferrule 416 by the use of adhesives, crimping, etc . . . Materials of fabrication for the shape memory portion 422 of delivery catheter 420 include Nitinol. In the normal unstressed condition of delivery catheter 420, memory portion 422 defines an arcuate orientation angularly oriented relative to the longitudinal axis as shown. In a preferred embodiment (e.g., in BPH application), memory portion 422 defines a radius of curvature "r" ranging between about 0.300 to about 0.500 inches, preferably about 0.400 inches. Delivery catheter 420 preferably has an outer diameter of about 0.04 inches. A Teflon™ shrink tubing 424 is preferably disposed about delivery tube 420 as best depicted in FIG. 7.

Bipolar electrode unit 406 is disposed within delivery catheter 420 and extends through handle 402 where it is connected to actuating portion 412 through ferrule 426. Ferrule 426 is fixedly mounted within a correspondingly dimensioned recess 428 (FIG. 22) formed in actuating portion 412. Through this arrangement, movement of actuating portion 412 causes corresponding translation of electrode unit 406 within delivery catheter 420.

Figures 5, 6:
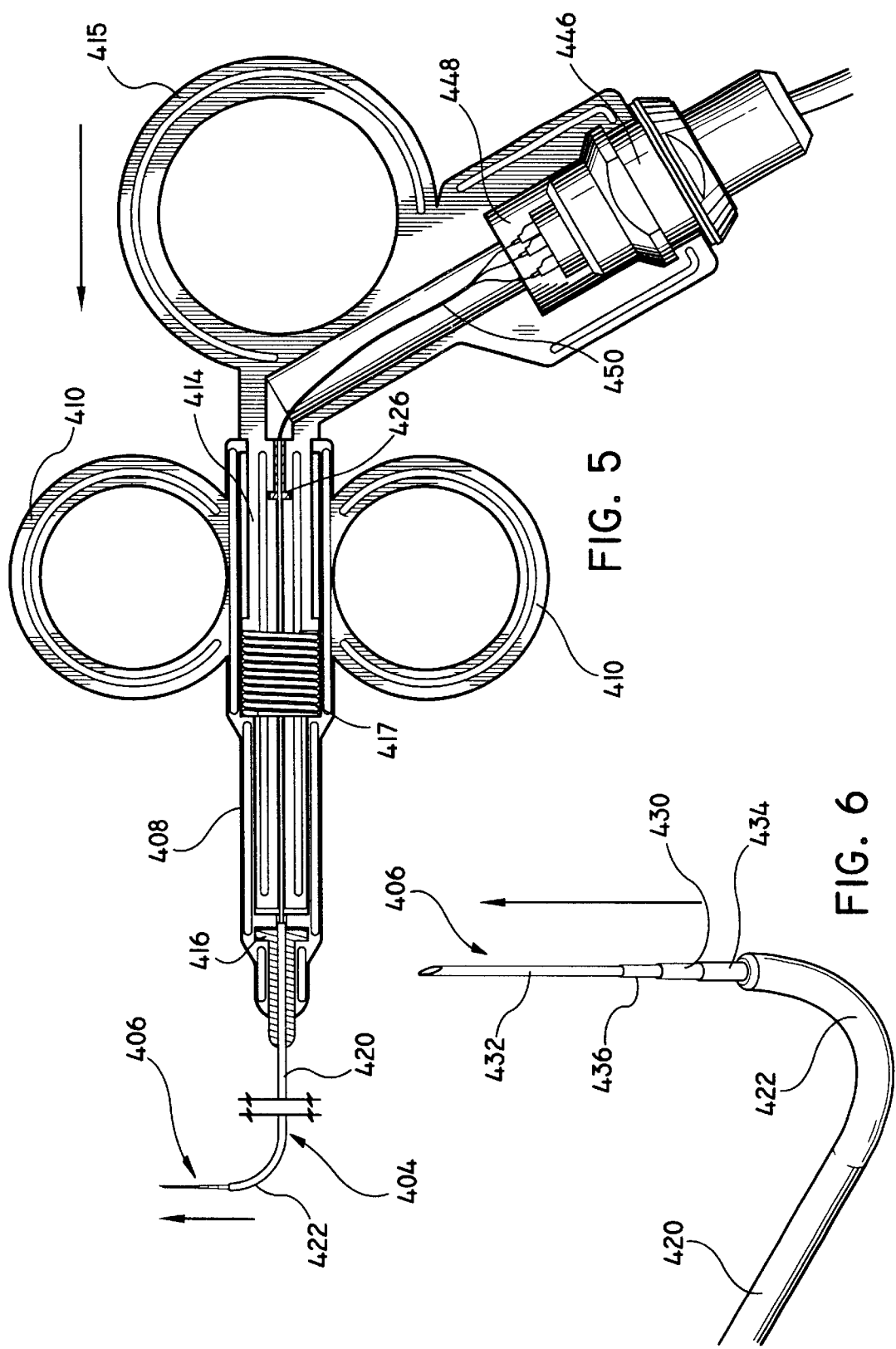
FIG. 5 is a view similar to the view of FIG. 3 illustrating actuation of the actuating portion to deploy the electrode assembly beyond the directional (delivery) tube of the elongate portion.
FIG. 6 is a view similar to the view of FIG. 5 further illustrating the electrode assembly deployed from the directional tube.

As best illustrated in FIGS. 6–7 which depict electrode unit or assembly 406 deployed via advancement of actuating portion 412, the electrode assembly 406 includes an outer tubular bipolar electrode 430 and an inner tubular bipolar electrode 432 coaxially mounted within the outer electrode 430. Inner bipolar electrode 432 extends distally beyond outer tubular electrode 430. Each electrode 430, 432 has insulating layers 434, 436 respectively. Inner electrode 432 is preferably a needle electrode having a sharpened penetrating end as shown.

Figure 10:
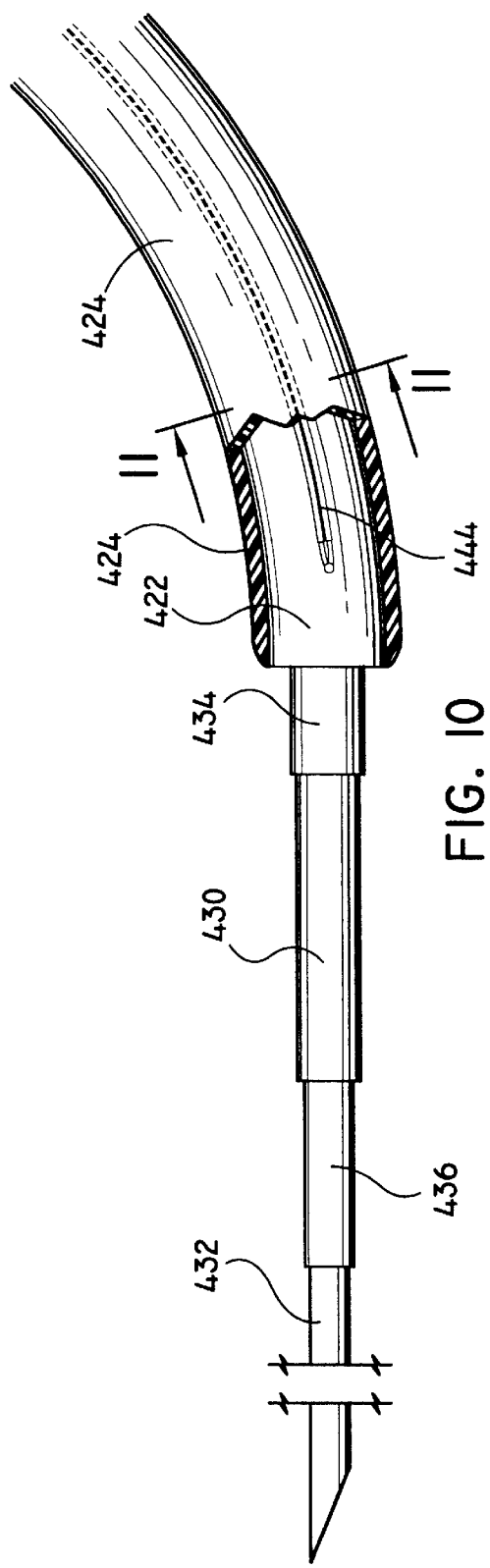
FIG. 10 is a side plan view of the distal end of the directional tube with portions cut away to depict a second thermocouple for detecting the temperature of tissue adjacent the treatment area.
Figure 11:
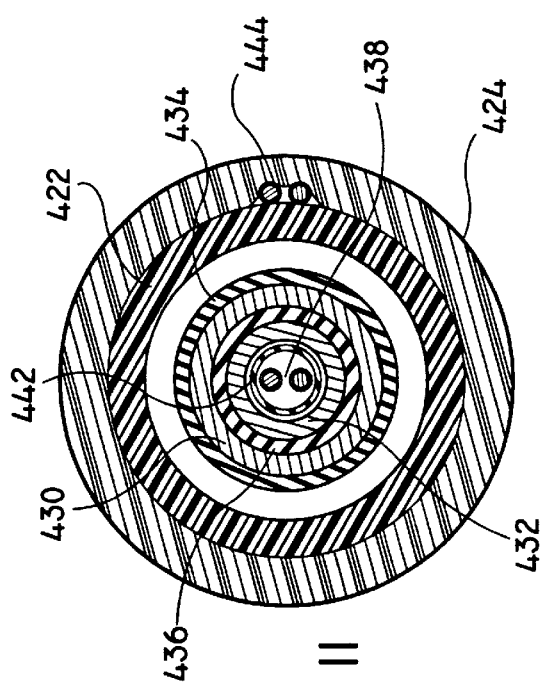
FIG. 11 is a cross-sectional view taken along the lines 11—11 of FIG. 10.
Figure 17:
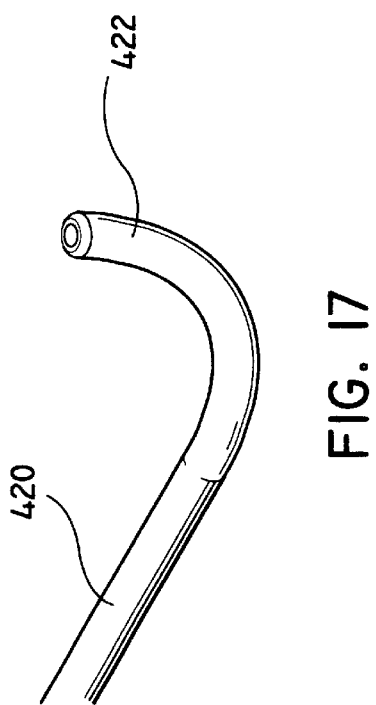
FIG. 17 is a view of an alternate embodiment of the auxiliary thermal treatment apparatus of FIG. 1 incorporating a monopolar electrode assembly.
Figure 18:
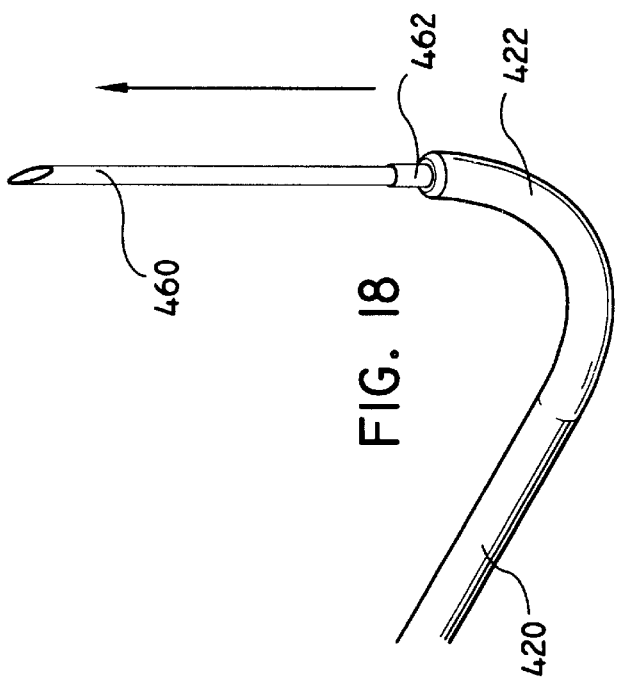
FIG. 18 is a perspective view of the distal end of the electrode assembly with the monopolar electrode deployed beyond the distal end of the directional tube.
Figure 19:
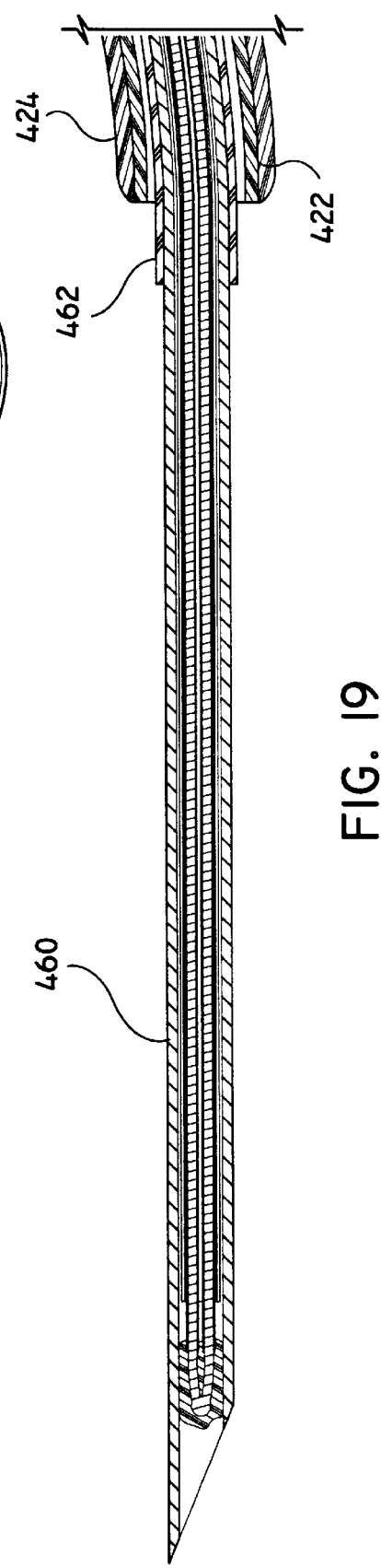
FIG. 19 is a cross-sectional view of the electrode illustrating a thermocouple disposed within the electrode for detecting the temperature of the treatment area.

Referring now to FIGS. 7–9, apparatus 400 further includes a first thermocouple 438 which extends within the axial bore of inner electrode 432. First thermocouple 438 is intended to measure the temperature of the tissue within the treatment area for monitoring purposes during the surgical procedure. An epoxy sealant 440 may be applied about the distal end of the thermocouple 438. First thermocouple 438 may be disposed within a protective sleeve 442 as shown. As depicted in FIGS. 10–11, a second thermocouple 444 may also be provided to measure the temperature of the tissue outside and adjacent the treatment area to ensure that this tissue is not undesirably thermally ablated. Second thermocouple 444 preferably extends between delivery catheter 420 and shrink tubing 424 which, as stated above, is wrapped about the outer surface of delivery catheter 420.

With reference again to FIGS. 2, 3 and 5, apparatus 400 further includes an electrical connector 446 which is mounted within a corresponding recess 448 in actuating portion 412 of handle 402. Connector 446 electrically connects the electrode assembly 406 and thermocouples 438, 444 to the RF energy source and the thermocouple accessory instrumentation, respectively, through appropriate wires 450. Instrumentation contemplated for use with thermocouples 438, 444 include a digital monitor to provide a readout of the temperatures ascertained with the thermocouples, as will be described hereinbelow.

Referring now to FIGS. 12–14, use of the apparatus 400 in connection with the thermal treatment of prostatic tissue to treat BPH will be discussed. Apparatus 400 is intended for use with a conventional scope such as cystoscope 200 which is identical to the cystoscope described in the '091 application and is insertable within a working channel of the scope through instrument port 216. In a preferred method of application, cystoscope 200 is initially inserted and advanced within the urethral passage "u" whereby the distal end of the scope is positioned adjacent the prostatic tissue to be treated. Auxiliary apparatus 400 is thereafter introduced through channel port 216 and advanced within the working channel. Alternatively, the apparatus 400 can be inserted through the working channel port 216 and the working channel, and the entire assembly inserted into the urethral passage. It is to be noted that memory portion 422 of delivery catheter 420 assumes a generally linear configuration upon insertion within the cystoscope working channel. Upon exiting the distal end of working channel 214, memory portion 422 assumes its normal unstressed curved orientation depicted in FIGS. 12–14. FIG. 12 illustrates memory portion 422 partially deployed while FIGS. 13–14 illustrate the memory portion 424 in the fully deployed position. As shown in FIG. 14, memory portion 422 will not penetrate the prostatic tissue upon deployment, but, rather will engage the inner wall of the urethra and bias the wall inwardly.

With reference now to FIGS. 15–16, actuating portion 412 is then advanced in the direction of the directional arrow of FIG. 15 to advance the electrode assembly 406, i.e., actuating portion 412 is advanced from the position depicted in FIG. 3 to the position depicted in FIG. 5. Upon deployment, the needle portion of inner electrode 432 pierces the urethral wall "u" to access the prostatic tissue "p". Electrode unit 406 is continually advanced whereby outer electrode 430 is disposed within the prostatic tissue and insulating layer 434 of the outer electrode 430 is adjacent the urethral lining. The system is thereafter energized whereby a thermal treatment region is created by transfer of RF energy between the outer and inner electrodes 430, 432.

The coaxial arrangement of the electrode assembly 406 reduces the overall diameter of the elongate portion 404 of the thermal treatment apparatus, thus, facilitating incorporability within a cystoscope. It is to be appreciated that the arrangement and lengths of the exposed electrodes 430, 432 (and thus insulation) may be varied to create other thermal treatment capacities.

FIGS. 17–21 illustrate an alternate embodiment of an auxiliary thermal treatment apparatus. This apparatus is similar in most respects to the prior embodiment, but, incorporates a monopolar electrode assembly having a single monopolar electrode 460 with insulating layer 462. The apparatus may be utilized with a grounding pad positioned adjacent the body as is conventional in the art. Delivery catheter 420 and memory portion 422 are substantially similar to the prior embodiment. A shrink tubing 424 is positioned about delivery catheter 420. As best Age depicted in FIGS. 20–21, thermocouple 438 is disposed within delivery catheter 420 and thermocouple 444 is disposed between the shrink tubing 424 and the outer surface of delivery catheter 420.

Referring now to FIGS. 22–23, an alternate embodiment of the monopolar thermal treatment apparatus of FIGS. 17–21 is illustrated. Apparatus 500 includes handle portion 502 having frame 504 and actuating portion 506 slidably mounted to the frame. Actuating portion 506 includes dual connectors, namely, electrode connector 508 and infusion port 510. Electrode connector 508 connects to a RF energy source. Infusion port 510 is preferably a luer-type connector and operatively connects to an infusion liquid or dissipating agent utilized to facilitate dissipation of the RF energy at the electrode end. Actuating portion 506 further includes thermocouple connector 512 which connects to one of the thermocouples of the instrument. Frame 504 of handle portion 502 includes a separate thermocouple connector 514 mounted thereto which electrically connects with a second thermocouple incorporated in the instrument. Actuating portion 506 is slidably mounted to frame 504 and is connected to the electrode unit in an identical manner to that described above. The remaining components are identical to their corresponding parts described in connection with the embodiment of FIG. 1. In accordance with this embodiment, other than the hollow passage discussed below, the electrode unit is substantially identical to that described in connection with the aforedescribed embodiment of FIGS. 17–21.

As depicted in FIGS. 25–27, a first thermocouple 516 extends between the outer shrink tubing 518 and delivery catheter 520 and is utilized to measure the temperature of the tissue adjacent the treatment area. First thermocouple 516 is electrically connected to electrode connector 508 of actuating portion 506. A second thermocouple 522 extends between insulating layer 524 and monopolar needle electrode 526 to detect the temperature of the tissue within the treatment area. Second thermocouple 522 is electrically connected to electrode connector 514 of frame 504.

FIGS. 26–27 also illustrate the dissipating agent or fluid 528, e.g., saline solution, which passes through the hollow passage of the electrode 526 as will be discussed.

Figure 24:
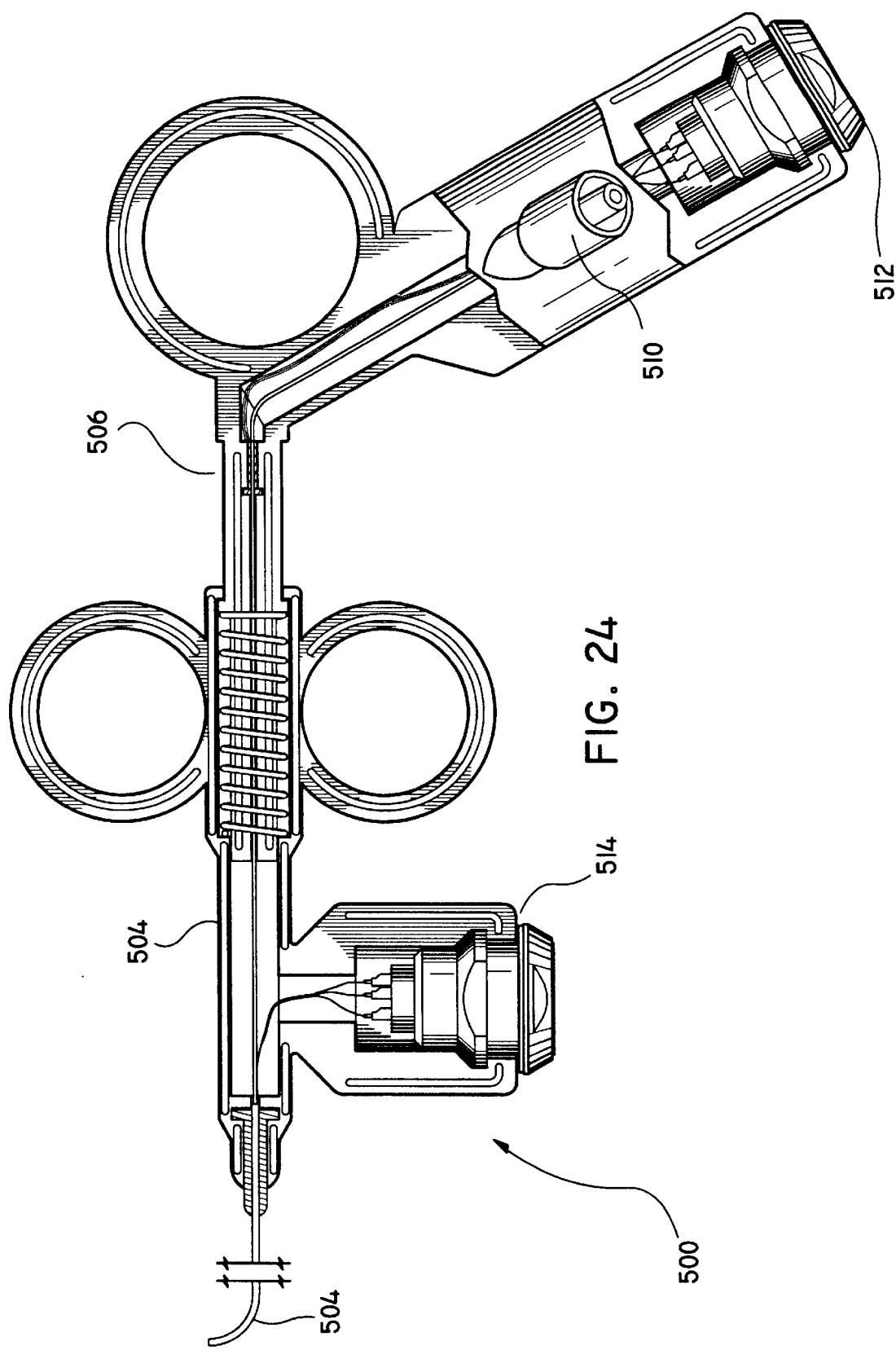
FIG. 24 is a side plan view of the apparatus with the handle in partial cross-section.
Figures 29, 30:
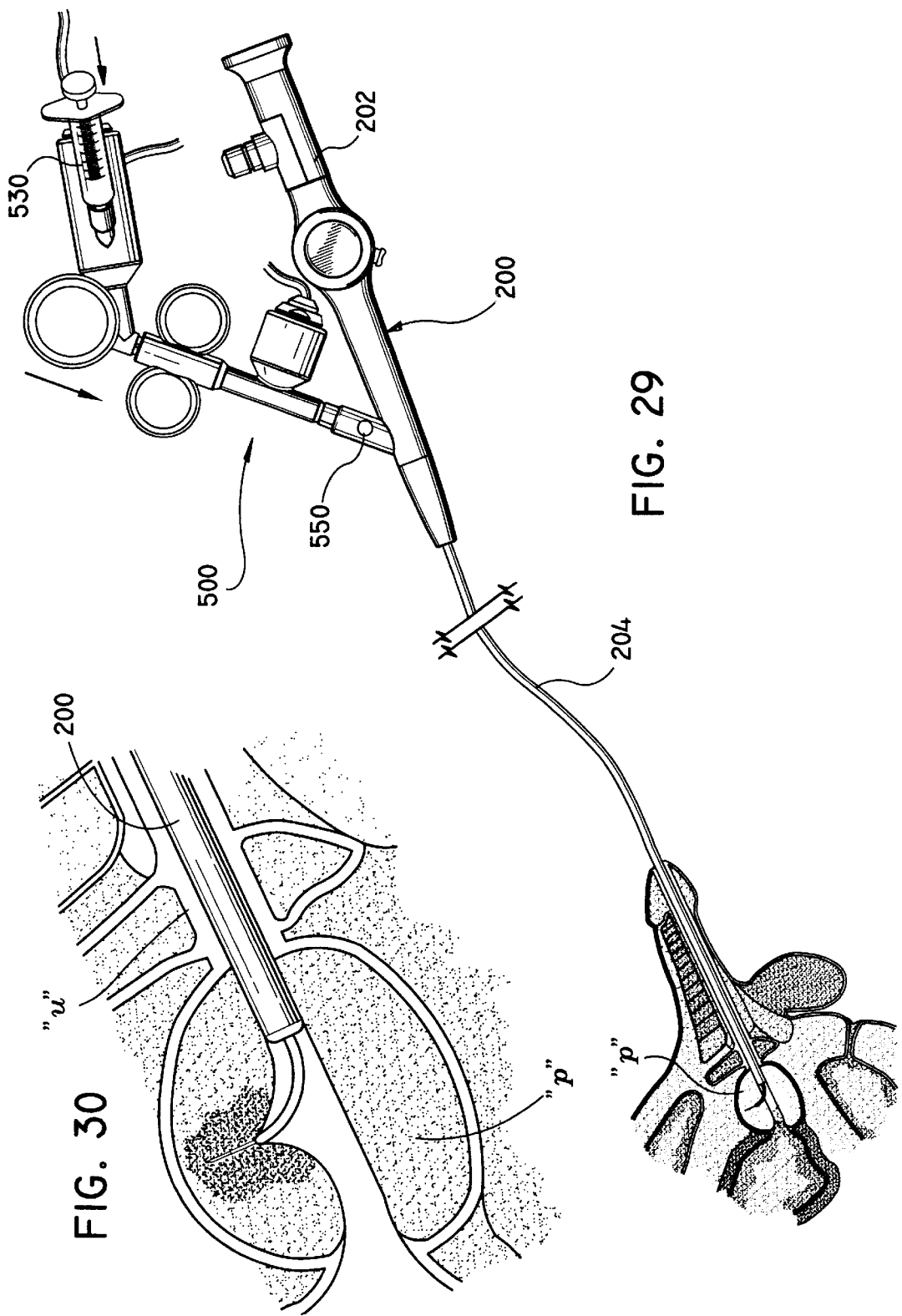
FIG. 29 is a view illustrating the cystoscope and mounted thermal treatment apparatus inserted within the urethral passage.
FIG. 30 is an isolated view illustrating deployment of the electrode assembly within the prostatic tissue.

With reference now to FIGS. 28–30, use of the apparatus 500 will be described. A syringe 530 containing the dissipating fluid, e.g. hypertonic saline solution, is connected to infusion port 510. In the alternative, a fluid bag may also be utilized and connected to the port in a conventional manner. With the cystoscope 200 accessing the urethral passage, the apparatus 500 is inserted and the needle electrode 526 is deployed by advancing actuating portion 506. Prior to and during treatment, i.e. energization of the system to apply RF energy saline solution is infused with syringe 530 through the hollow passage of electrode 526 and into the treatment site to facilitate dissipation of the thermal energy and to assist in focusing the current on the target tissue. Preferably, a tube 532 is provided FIG. 24) to fluidly connect port 510 and the inner passageway of electrode 526. During treatment, the temperature of the treatment area and area adjacent the treatment area may be monitored with thermocouples 516, 522. Other fluids can be injected through the hollow passage of electrode 526 such as an anesthetic agent or drug post op to minimize edema.

Port 550 can be provided for suction or irrigation, e.g. injection of isotomic saline in the working channel in the space surrounding the delivery tubes.

Figure 31:
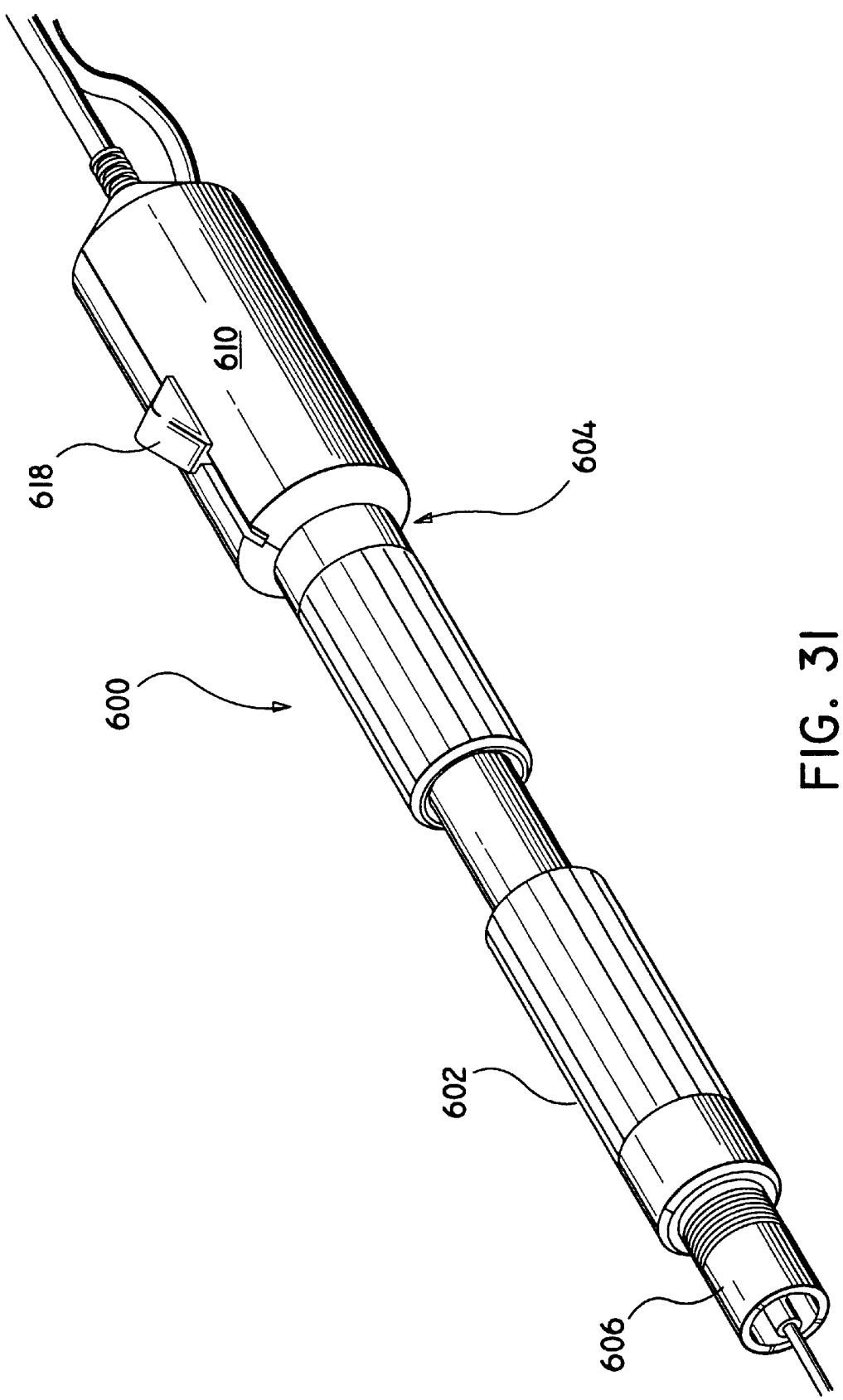
FIG. 31 is a perspective view of an alternate embodiment of a handle to be utilized with the monopolar electrode embodiments of FIGS. 17–28.
Figure 32:
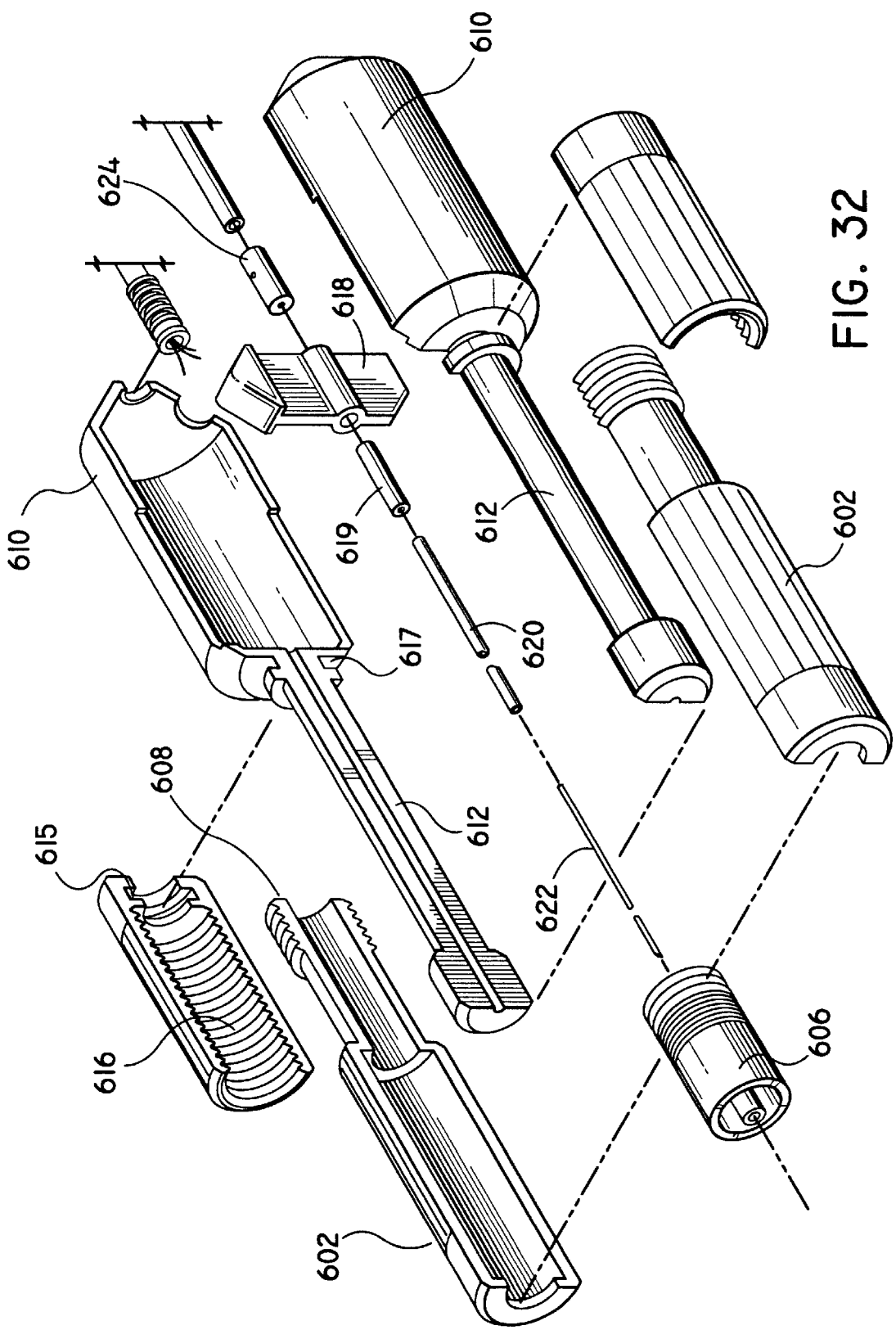
FIG. 32 is a perspective view with parts separated of the handle of FIG. 31.
Figure 33:
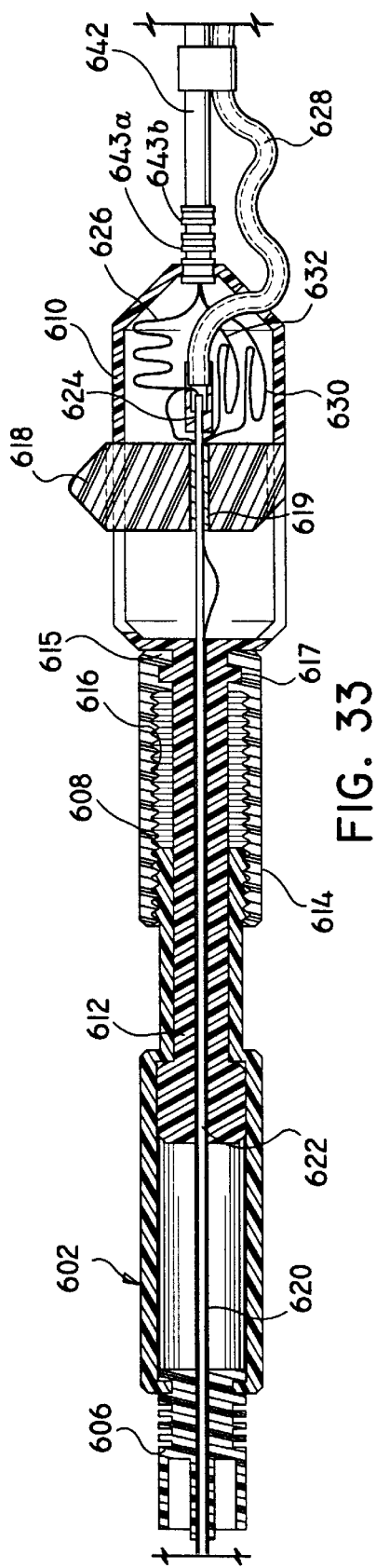
FIG. 33 is a side cross-sectional view of a handle in an unactuated position.

Referring now to FIGS. 31–33, there is illustrated an alternate handle of the apparatus of the present disclosure. Handle 600 is contemplated for use with a monopolar electrode assembly, e.g., those depicted in FIGS. 17–21 and FIGS. 22–28. Handle 600 includes stationary housing portion 602 and movable housing portion 604 which is longitudinally moveable relative to stationary housing portion 602. Stationary housing portion 602 has a mounting collar 606 mounted at its distal end which supports the elongate body of the apparatus. Stationary housing portion 602 further defines at its proximal end a threaded portion 608. Movable portion 604 includes a frame 610 and an elongated drive portion 612 extending from the frame 610. The elongated drive portion 612 is at least partially accommodated within the axial bore of stationary housing 602 and is adapted to move within the stationary housing 602 to deploy the delivery catheter as will be discussed.

A rotatable control member 614 is coaxially mounted about elongated drive portion 612. Rotatable control member 614 is longitudinally fixed with respect to movable housing portion 604 through an interfitting relationship of a locking groove and collar arrangement. More particularly, rotatable control member 614 includes a collar 615 which fits within a groove 617 of movable hosing portion 604 to longitudinally fix the rotatable control member 614 to the movable housing portion 604. Rotatable control member 614 has an internal thread 616 which cooperates with threaded portion 608 of stationary housing 602 to longitudinally move the movable housing portion 604 upon rotation of the control member 614.

A deployment member 618 is mounted within the main frame 610 of movable housing 604 and is adapted to move longitudinally with respect to the movable housing portion 604. As will be appreciated from the description provided below, deployment member 618 is connected to the electromagnetic probe and functions in deploying the probe from the distal end of the delivery catheter.

Referring particularly to FIG. 33, in view of FIG. 32, the interrelationship of the delivery catheter and electromagnetic probe with the components of handle 600 will be discussed. The delivery catheter and electromagnetic probe are identical to the delivery catheter and probe discussed in connection with the embodiment of FIG. 17 or in the embodiment of FIG. 22. Delivery catheter 620 extends within handle 600 and through an axial bore of movable housing 604. The proximal end of delivery catheter 620 is longitudinally fixed to elongated portion 612 of movable housing portion 604. Any conventional means for securing delivery catheter 620 to elongated drive portion 612 may be utilized including welding, cements, adhesives, etc . . . Accordingly, upon movement of movable housing portion 604 in the longitudinal direction as effectuated through rotation of rotatable control member 614, the delivery catheter 620 also moves longitudinally.

Electromagnetic probe 622 extends through delivery catheter 620 whereby the proximal end of the electromagnetic probe 622 continues within the main frame 610 of the movable housing portion 604. The proximal end of the electromagnetic probe 622 further extends through collar 619 mounted within deployment member 618 and terminates within a ferrule connector 624 disposed proximal of the deployment member 618. Electromagnetic probe 622 is longitudinally secured to collar 619 which is fixed to deployment member 618 such that movement of the deployment member causes corresponding longitudinal motion of the electromagnetic probe. Ferrule connector 624 is preferably mounted within a longitudinal recess or groove defined in the frame of the movable housing portion 604. Ferrule connector 624 is fixed to the proximal end of electromagnetic probe 622 by conventional means including welding, cements, adhesives, etc . . . and serves to provide the electrical connection between the electromagnetic probe 622 and the service line or cable 626 which supplies the electromagnetic energy from the energy source. Ferrule connector 624 also serves in receiving the saline solution tube 628 to connect the tube to the interior lumen extending within the electromagnetic probe 622.

Also depicted in FIG. 33 are the source lines servicing the two thermocouples. In particular, the first line 630 services the thermocouple extending between the outer shrink tubing and delivery catheter (see discussion in connection with embodiment of FIGS. 17–22) which detects or measures the temperature of tissue adjacent the tissue area. The second line 632 services the thermocouple which extends within the electromagnetic probe 622 for detecting the temperature of the tissue in the treatment area.

Figure 35:
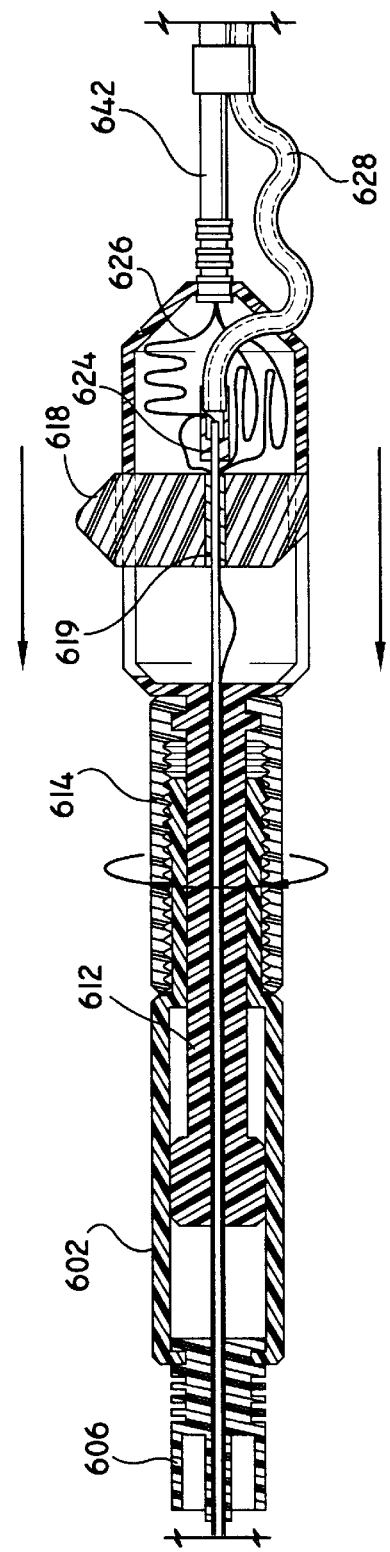
FIG. 35 is a view similar to the view of FIG. 33 illustrating rotation of the control member to selectively deploy the delivery catheter.
Figure 34:
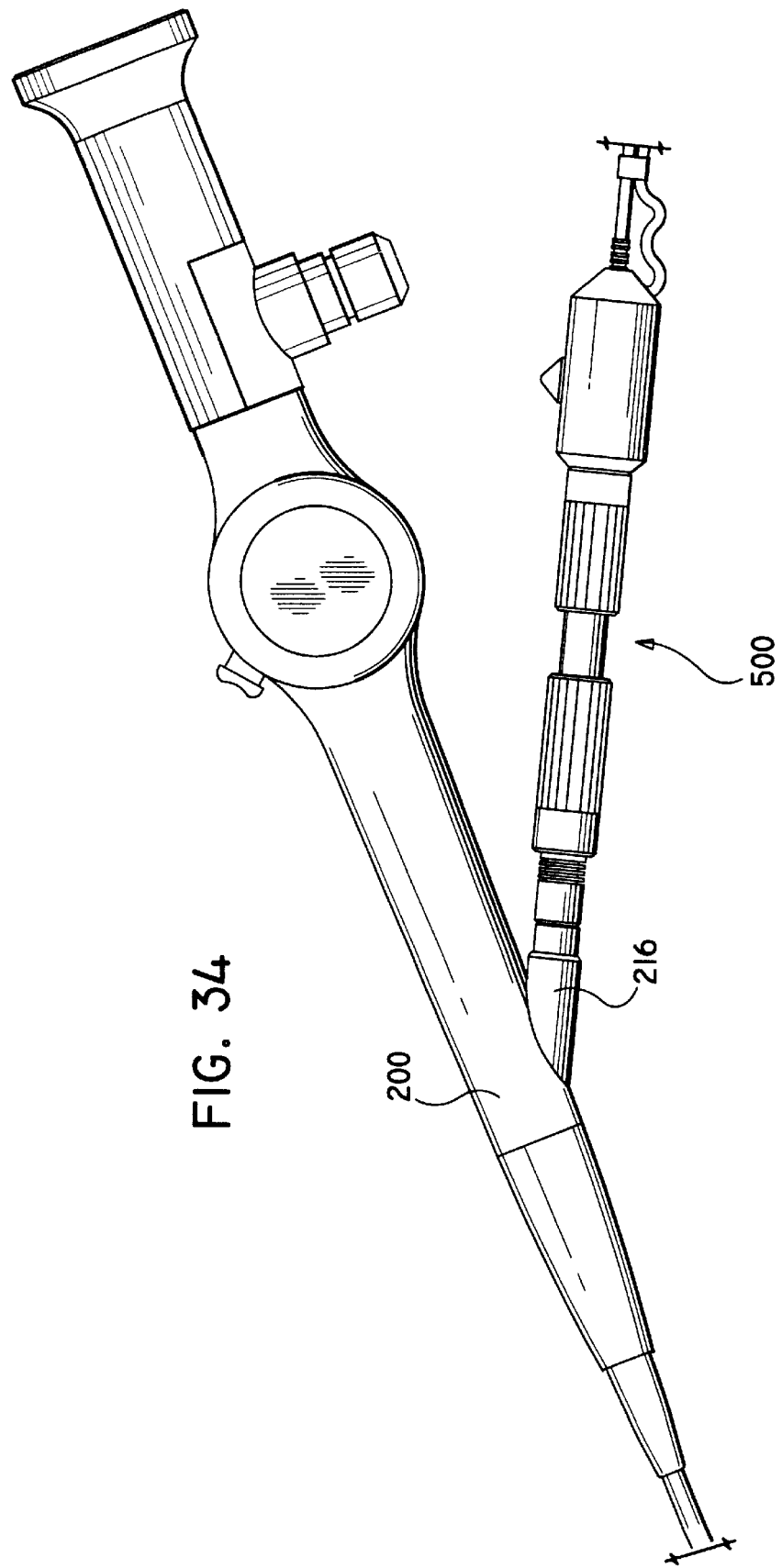
FIG. 34 is a side plan view of the handle of FIG. 31 mounted to a cystoscope.

Referring now to FIG. 34 the use of the apparatus will be discussed. With the cystoscope 200 accessing the urethral passage as discussed above, the elongated portion of the apparatus is inserted within the working channel of the scope and advanced until the handle engages the working channel port connector 216 extending from the proximal end of the working channel of the cystoscope as depicted in FIG. 34. Preferably, handle 600 includes a Luer type connector at its distal end which releasably engages the port connector 216. With reference to FIG. 35, the delivery catheter 620 is deployed by rotating the rotatable control member 614 in the direction depicted in FIG. 35. As rotatable control member 614 rotates the movable housing portion 604 advances through the threaded engagement of the threaded portions 608, 616 of rotatable control member 614 and the stationary housing 602 thereby advancing the delivery catheter 620 within the elongated portion of the apparatus and beyond the distal end of the working channel of the scope 200. It is appreciated that the rotatable control member 614 can be selectively incrementally rotated to provide selective incremental deployment of the delivery catheter 620, thus, providing enhanced control over the amount of deployment of the memory portion thereof. In effect, therefore, the angular orientation of the distal end of the delivery catheter 620 can be varied through the amount of deployment of the memory portion to achieve desired paths of entry into urethral tissue.

Figure 36:
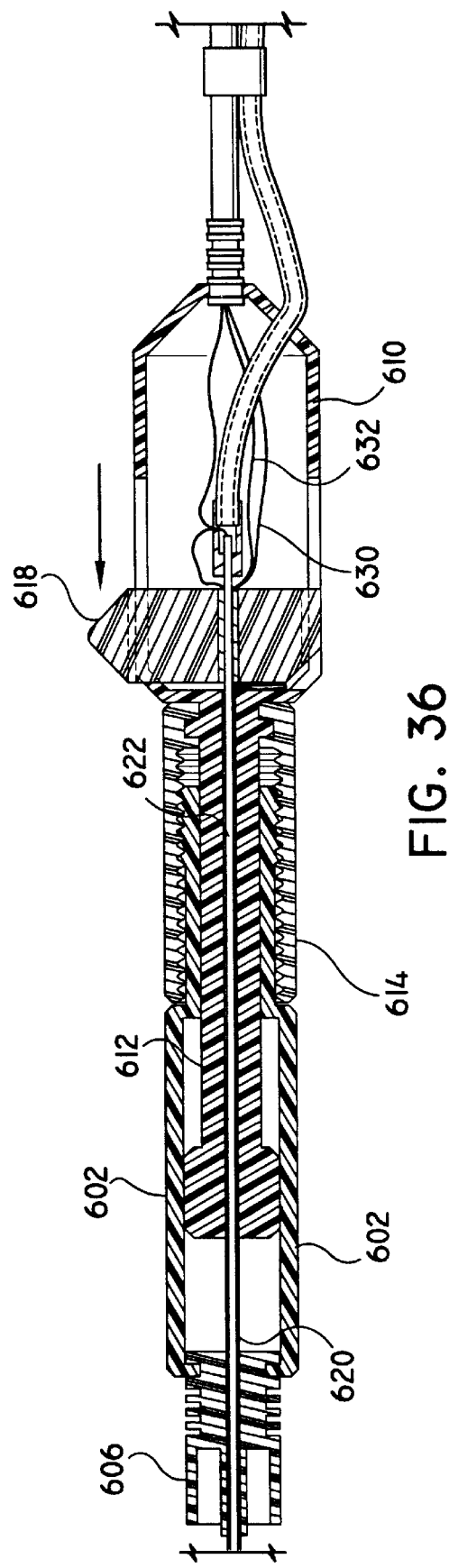
FIG. 36 is a view similar to the view of FIG. 33 illustrating the deployment member advanced to deploy the electromagnetic probe.

Once the delivery catheter 620 is deployed as desired, attention is directed to deploying electromagnetic probe 622. With reference now to FIG. 36, deployment member 618 is advanced in the direction of the directional arrow to deploy the electromagnetic probe 622 from the end of the deployment catheter. As the deployment member 618 moves in the longitudinal direction, the ferrule connector 624 is also carried longitudinally due to the fixing of the proximal end of the electromagnetic probe and the ferrule connector 624 as discussed above. It is to be noted that the service lines 626, 630 and 632 servicing both the thermocouples and the electromagnetic probe 622 have sufficient slack to permit advancing movement of the deployment member 618. Lines 626, 630 and 632 extend from handle 600 into a cable 642 that originates from a control unit (to be described below). Fluid line 628 originate from the control unit which controls the flow rate during the procedure. Optionally, cable 642 may have a connector 643b that mates with a connector 643a on handle 600 to permit manual attachment of cable 642 to handle 600.

It is also envisioned that the auxiliary apparatus described above can be used other than with a scope. For example, the delivery (directing) tubes can be inserted directly into the urethra or other body lumens. The tubes and electrodes can be monitored by ultrasound, MRI, fluoroscopy or other imaging techniques. Ultrasound can also be used in conjunction with the endoscope to image the needles in the adenoma. Further, the auxiliary apparatus may be used to thermally treat the BPH condition via the patient's rectum rather than via the urethra. To implement this procedure, the catheter/treatment electrode can be inserted within the working channel of a transrectal ultrasound TRUS) instrument, where the TRUS instrument is used to help guide the catheter to the proper location adjacent the prostate.

II. System

An exemplary embodiment of a system in accordance with the present disclosure will now be described a BPH thermal therapy system, including a controller and auxiliary treatment apparatus operating in a monopolar operating mode. However, it is understood that the system disclosed herein may be used with other thermal treatment instruments such as the bipolar instrument described above or those in the '091 application. In addition, the system may be used in surgical procedures other than for treatment of the BPH condition.

Figure 37:
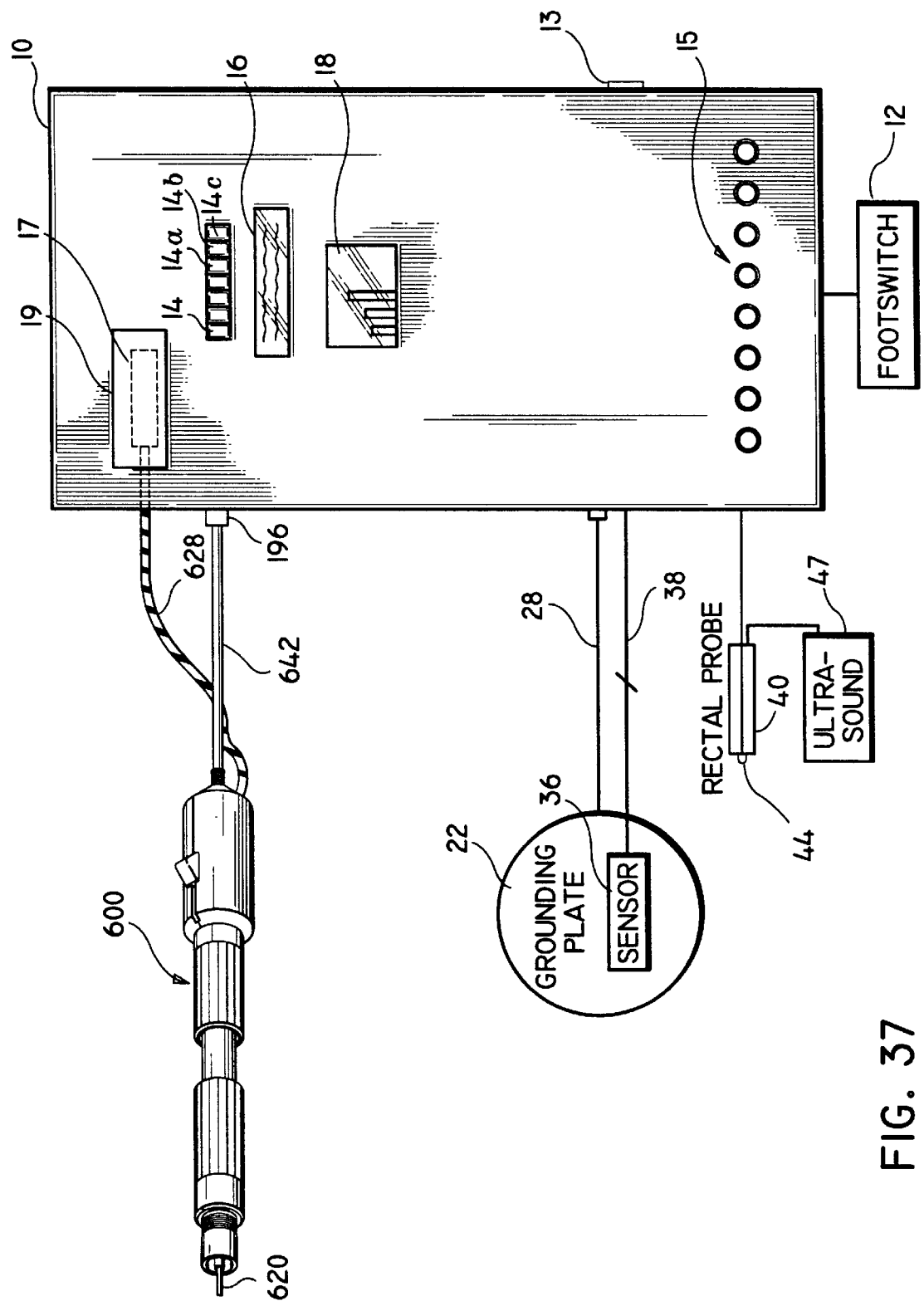
FIG. 37 schematically illustrates a BPH treatment system of the present disclosure.

Referring now to FIG. 37, an exemplary BPH therapy system in accordance with the present disclosure includes an RF generator/controller 10, handle/electrode assembly 600 (described hereinabove) and a grounding plate 22 positioned in abutting relation to the patient's body during BPH treatment. Assembly 600 includes the delivery catheter 620 which may be inserted directly into the patient's urethral passage and advanced by means of deployment member 618. Optionally, a cystoscope (not shown) may be used in conjunction with assembly 600, in which case the delivery catheter 620 is inserted into the working channel of the cystoscope, and the cystoscope working channel is inserted into the urethral passage. Generator/controller 10 includes an RF current generator to produce high frequency RF power (e.g., 50 watts output at 500 KHz) upon command from a processor within controller 10. The RF current is provided between the monopolar needle electrode within catheter 620 and the grounding plate 22, the latter typically being held against the patient's back. Current is caused to flow within the resistive human tissue between the monopolar electrode and grounding plate 22, to thereby thermally treat (e.g., ablate, vaporize or cauterize) the targeted prostatic tissue. Since the electrode has a much smaller surface area than the grounding plate, the current flowing in the vicinity of an exposed distal portion of the electrode is much higher in intensity than at the grounding plate. As a result, by using an appropriate RF power level, only the prostate tissue in the vicinity of the electrode is thermally treated while other body tissue in between the electrode and the grounding plate carries a low enough current to remain unperturbed. As a result of this treatment, the targeted prostatic tissue necroses and dies, thus, relieving pressure off the urethral wall and alleviating the symptoms of BPH. The ablation of the targeted prostatic tissue is facilitated by infusing hypertonic saline into the treatment area through catheter 620. The hypertonic saline functions to increase the effective treatment zone. The hypertonic saline essentially acts as a large electrode which is "activated" by "plugging in" the monopolar needle electrode. The size and speed in which a thermal lesion can be created is a function of the infusion rate, the amount of saline delivered prior to RF power delivery, the saline concentration and the magnitude of RF power delivery. Accordingly, combining intraprostatic infusion of hypertonic saline and radio frequency energy delivery allows tissue destructive thermal lesions to be quickly created (e.g., in 30–75 seconds) without need for multiple applications.

In addition, the saline solution serves to allow a more uniform ablation of the targeted prostate tissue and also to prevent charting of the tissue against the monopolar electrode surface. Such charring would otherwise present a high impedance at the electrode surface which would inhibit ablation of a desired volume of prostate tissue.

As discussed above, patient cable 642 includes two pairs of thermocouple wires and a wire that connects to the monopolar electrode. Cable 642 has a connector on its end to allow manual connection to connector 196 on the controller housing. Saline line 628 connects to a disposable syringe 17 mounted within controller 10, where syringe 17 is removable through a hatch door 19 on the controller housing. Saline flow from syringe 17 is automatically induced by means of a processor-controlled saline pump within controller 10. Prior to the insertion of catheter 620 into the patient, a "purge" operation is performed to remove air from the saline line. During the purge operation, which is initiated by manual depression of a purge switch 14c, saline is caused to flow at a constant rate, e.g., 4 cc/minute. After catheter 620 is inserted within the patient and the footswitch is depressed, saline is caused to flow at a constant rate, e.g. 2 cc/minute, during both a pre-infusion period (e.g. 30 seconds) in which no RF energy is applied, and also during the time period of RF power treatment.

Grounding plate 22 is connected to a return line 28 which completes the RF current path from the monopolar electrode. An optional continuity sensor 36 may be mounted on grounding plate 22 to sense improper surface contact of the grounding plate against the patient and to provide a corresponding signal on lines 38 to controller 10. The quality of the ground plate contact with the patient may be determined based on the magnitude of the return signal from sensor 36. An alarm may be sounded if patient continuity between two or more points on the ground plate is unsatisfactory. The processor would automatically cause termination of RF power delivery when this alarm condition occurs.

An optional rectal probe 40 includes a thermistor 44 to sense rectal temperature. Controller 10 displays rectal, prostate and urethral temperatures during the BPH treatment procedure on a color bar display 18 and also on an alphanumeric display 16. Rectal probe 40 is attached on the side of an ultrasound instrument 47 including a display to allow the operators to see and control the position of catheter 20 within the urethra. This enables the physician to make a determination of what volume of prostate tissue should be thermally treated. The processor automatically causes termination of RF power delivery if the rectal temperature exceeds a predetermined threshold.

Controller 10 also includes push button switches 14 to permit user-control of various aspects of the treatment. Among the switches 14 are several "treatment volume" switches, each of which corresponds to a selected target volume of prostate tissue to be ablated during the subsequent treatment (i.e., the volumetric size of the thermal lesion to be created). The targeted treatment volume is presumed to be reached as soon as a specific treatment time, i.e., a specific time duration of RF power delivery corresponding to that treatment volume, is reached. Exemplary treatment times are 30, 45 and 75 seconds for treatment volumes of <4 cm$^3$, 4–8 cm$^3$ and >8 cm$^3$, respectively. The RF output power is automatically turned off by the controller when the treatment time is reached. If, however, the measured prostate or urethral temperature exceeds a safety limit. e.g., 104° C., prior to the treatment time being reached, RF power automatically shuts off.

Also included among switches 14 are a "pump retract" switch 14a, a "pump advance" switch 14b and the aforementioned purge switch 14c, each of which control the position of a push rod connected to the saline pump. Switch 14a facilitates replacement of the syringe. Switch 14b is depressed in order to advance a pushing rod against a plug within the syringe. Depression of purge switch 14c causes saline to flow prior to RF current delivery. The purge switch 14c is depressed in the pre-operative procedure, mentioned above, to cause saline flow through catheter 620 before the catheter is inserted into the patient, in order to remove any air that may be present. Once the purge button is released, saline flow ceases.

Controller 10 also includes a connection to pneumatic footswitch 12 which initiates the start of treatment when depressed. LEDs 15 are included to provide visual indications of various alarm conditions. An RS 232 connector 13 enables connection of controller 10 to an external computer such that unit software can be uploaded and log files of treatments performed can be downloaded from controller 10 to the computer.

At the outset of a treatment, controller 10 performs a self-test. The operator purges the saline prior to inserting catheter 620 within the patient by depressing the purge switch 14c. After a first treatment is complete (i.e., after the predetermined treatment time corresponding to the treatment volume is reached) the operator has the option to treat another portion of the prostate (or other tissue being treated) by manipulating the catheter 620 and the monopolar electrode position. Once the new position is selected, the operator then depresses a "re-start" button on the controller 10 housing. When the restart button is depressed, the purge switch 14c is preferably disabled. The operator then once again selects a treatment volume. Then, the new treatment area is pre-infused for, e.g., 30 seconds when the footswitch is depressed. The saline is also caused to flow during the new treatment as RF is applied in the same manner as in the first treatment. Additional treatments are also contemplated by pressing the re-start button again in the above-described manner.

Figure 38:
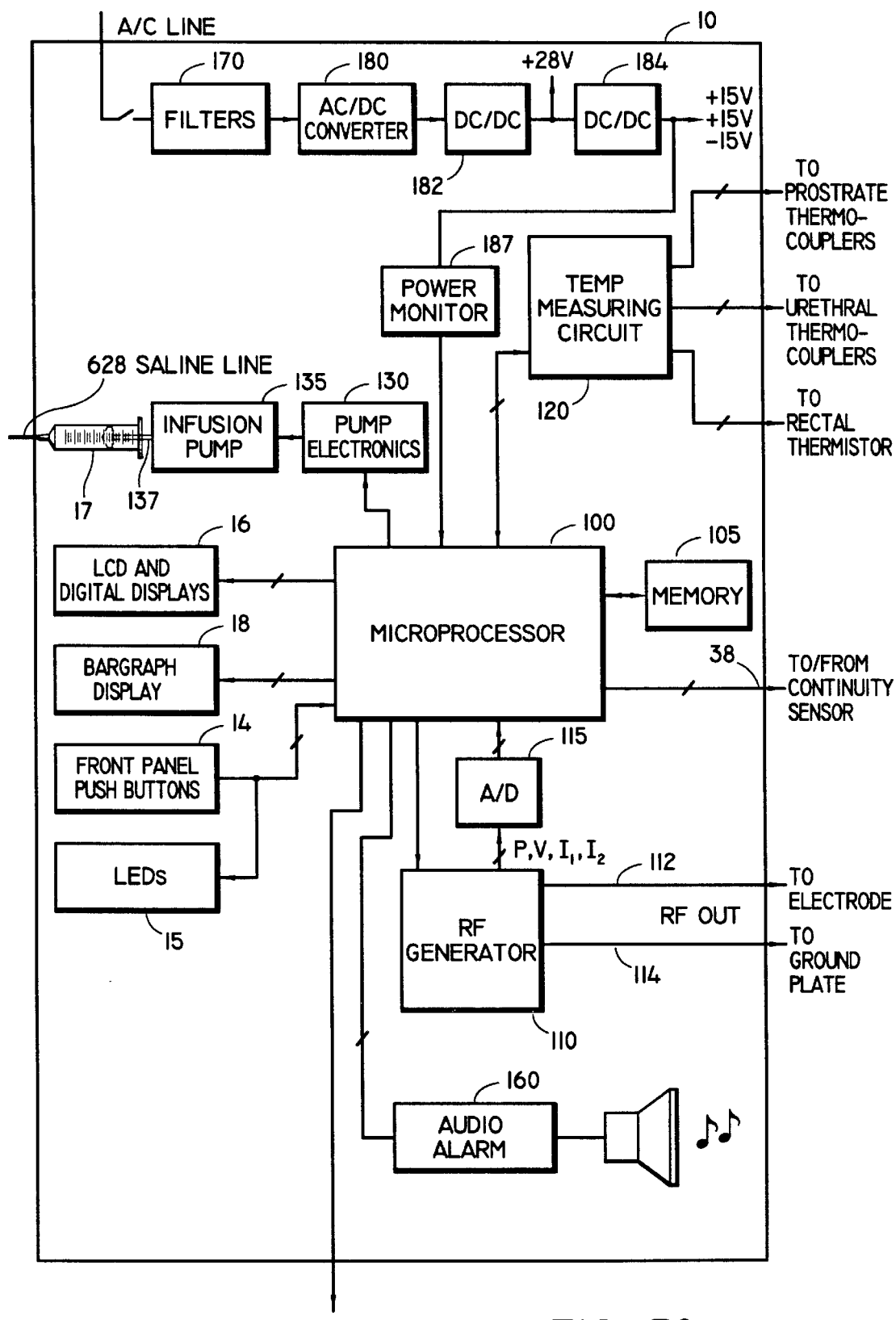
FIG. 38 is a block diagram showing hardware components within the controller of the present disclosure.

With reference now to FIG. 38, a simplified block diagram of exemplary electronics within RF generator/controller 10 is shown. A microprocessor 100 includes memory 105 which stores the software program controlling the BPH therapy procedure. Memory 105 also stores log files for each treatment performed for subsequent uploading to an external computer. An RF generator 110 connects to ablation electrode 24 and to ground plate 22 and outputs RF current therebetween upon command from microprocessor 100. When the RF power is turned on, circuitry within RF generator 110 measures the output power P, voltage V between its output leads 112 and 114, forward current II on lead 112 and return current I2 on lead 114. Analog signals corresponding to these parameters are forwarded to an analog to digital (A/D) converter 115 where they are digitized and provided to processor 100. The impedance between lines 112 and 114 is computed periodically (e.g., every second) by microprocessor 100 based on these signals. This impedance corresponds substantially to the impedance between electrode 24 and ground plate 22 in contact with the patient, and is typically in the range of 35–300 ohms under normal conditions. An excessively high impedance may indicate that undesirable charring is present on the surface of the ablation electrode. If the impedance exceeds a predetermined value stored in memory (e.g. 300 ohms) then RF current flow is terminated via a command from processor 100 to RF generator 110. In addition, if impedance is below a predetermined threshold, RF current flow is terminated via a command from processor 100. Microprocessor 100 also activates an audio alarm 160 when a high or low impedance condition occurs during the course of treatment.

For each BPH treatment, microprocessor 100 writes various information into the log file of memory 105. Data corresponding to at least the following items are written into the log file for subsequent downloading to an external computer: date; time of start session; treatment volume selected; time stamp; prostate temperature; urethra temperature; rectal temperature; impedance; return current; and forward current and power. The data is written into the log file at periodic intervals, e.g., every second, during the course of treatment.

As mentioned above, saline solution (preferably, hypertonic saline solution) is stored within disposable syringe 17 mounted within controller 10. Microprocessor 100 controls the saline flow by providing commands to pump electronics 130 which in turn control an infusion pump 135. Pump 135 drives a ram 137 at a controlled rate during the treatment to provide a constant saline flow.

A temperature measuring circuit 120 is coupled to the prostate and urethral thermocouples and to the rectal thermistor. Circuit 120 sends temperature data to microprocessor 100 corresponding to the temperatures sensed by the respective sensors. Microprocessor 100 displays the current prostate, urethral and rectal temperatures on digital display 16 as well as on bar graph display 18. As mentioned above, the user selects a treatment volume by depression of one of the front panel push buttons 14. For each treatment volume, specific treatment times are stored in memory 105. By way of example, the user may select one of three treatment volumes, e.g., less than 4 cm$^3$, 4 cm–8 cm$^3$, or greater than 8 cm$^3$. Corresponding treatment times stored in memory 105 may be 30, 45 and 75 seconds, respectively. During the treatment, if a threshold temperature corresponding to a safety limit is reached at either the urethra, prostate or rectum, processor 100 commands RF generator 110 to shut off the RF output power, thus terminating any further RF ablation. These safety limits are preferably fixed for the respective prostate, urethra and rectal regions, regardless of the treatment volume selected. In addition, if the circuitry determines that any of the thermocouples is open, RF output power will be automatically shut off and an alarm will be generated.

As an alternative to allowing user-selection from one of several treatment volumes, the software can be modified by storing a simple algorithm that computes a treatment time as a function of a user-inputted treatment volume. User input may be through a computer connected to port 13 or through a keypad input on the controller 10 housing.

Optionally, to provide an additional safeguard, an independent hardware timer clock can be provided, which would be active whenever the RF energy is on. This clock is continuously polled, and if the cumulative time that the RF energy has been applied during the procedure exceeds a predetermined threshold, the controller automatically shuts off the RF energy.

As an alternative to terminating the treatment when the treatment time corresponding to the treatment volume is reached or if a safety temperature limit is reached, treatment temperatures corresponding to each treatment volume can be stored in the controller memory, and the controller software can designed to terminate treatment as soon as the treatment temperature is reached. For this embodiment, a safety treatment time would preferably be stored in memory, and the treatment would be automatically terminated if the treatment time is reached prior to the treatment temperature being reached. This safety treatment time could be different for the respective treatment volumes.

Controller 10 operates off AC line voltage which is filtered to reduce noise by filters 170 and converted to DC by AC/DC converter 180. The DC voltage is stepped down to +28V and isolated by DC/DC converter 182. RF generator 110 and pump electronics 130 are each fed the +28V for operating voltage. Another DC/DC converter 184 is utilized to step down the +28V to lower voltages (+5V, +15V, −15V) which are used to power the other electronics of controller 10. A power monitor 187 monitors the lower voltages and provides signals to microprocessor 100 indicative of whether the voltages are within predetermined tolerance ranges. To minimize the possibility of electric shock to the patient, the +28V DC is isolated from the patient by using opto-couplers or other isolation measures between the components contacting the patient and the electronics operating with +28V.

Figure 39:
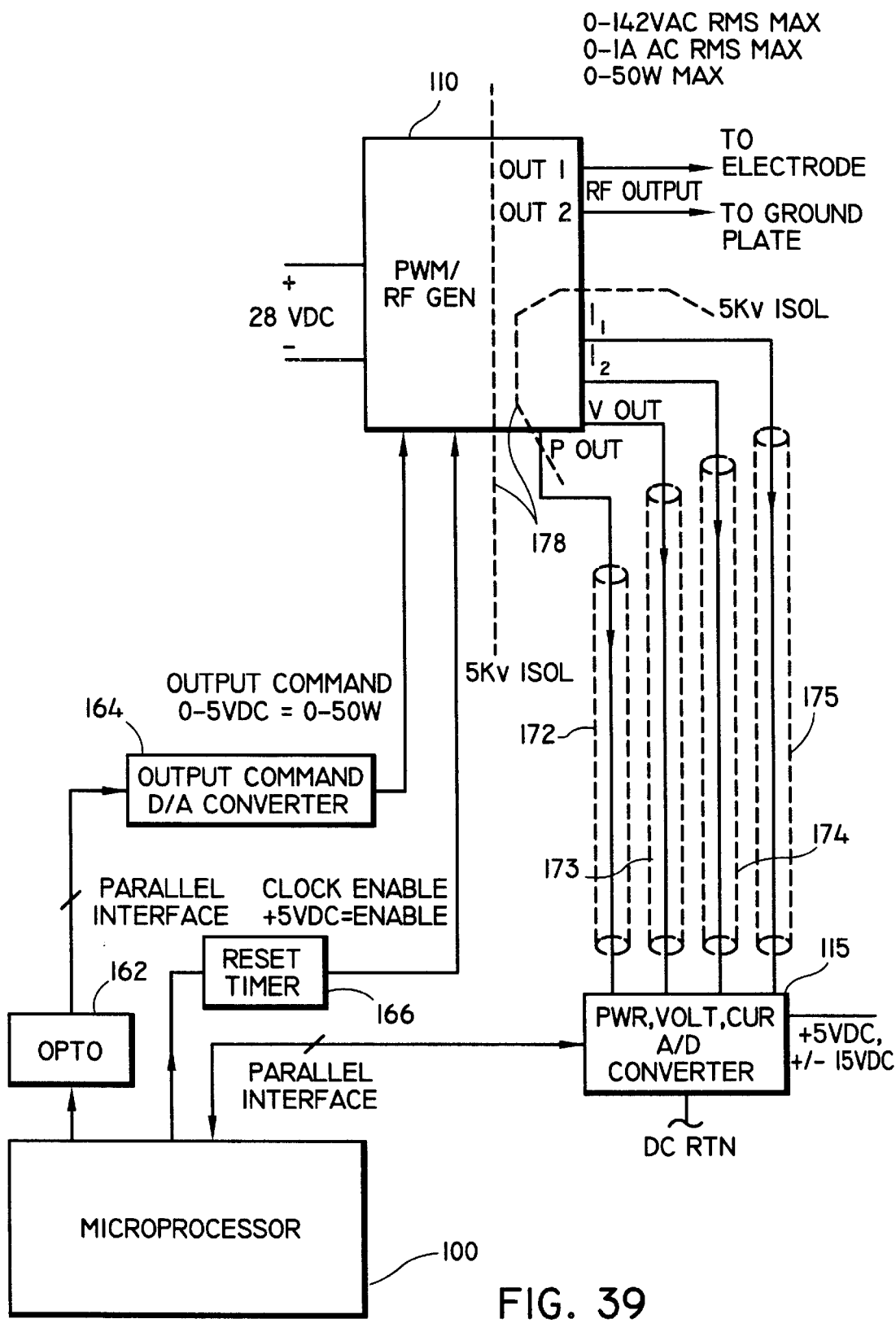
FIGS. 39–41 are schematic block diagrams of specific hardware portions within the controller hardware.
Figure 40A:
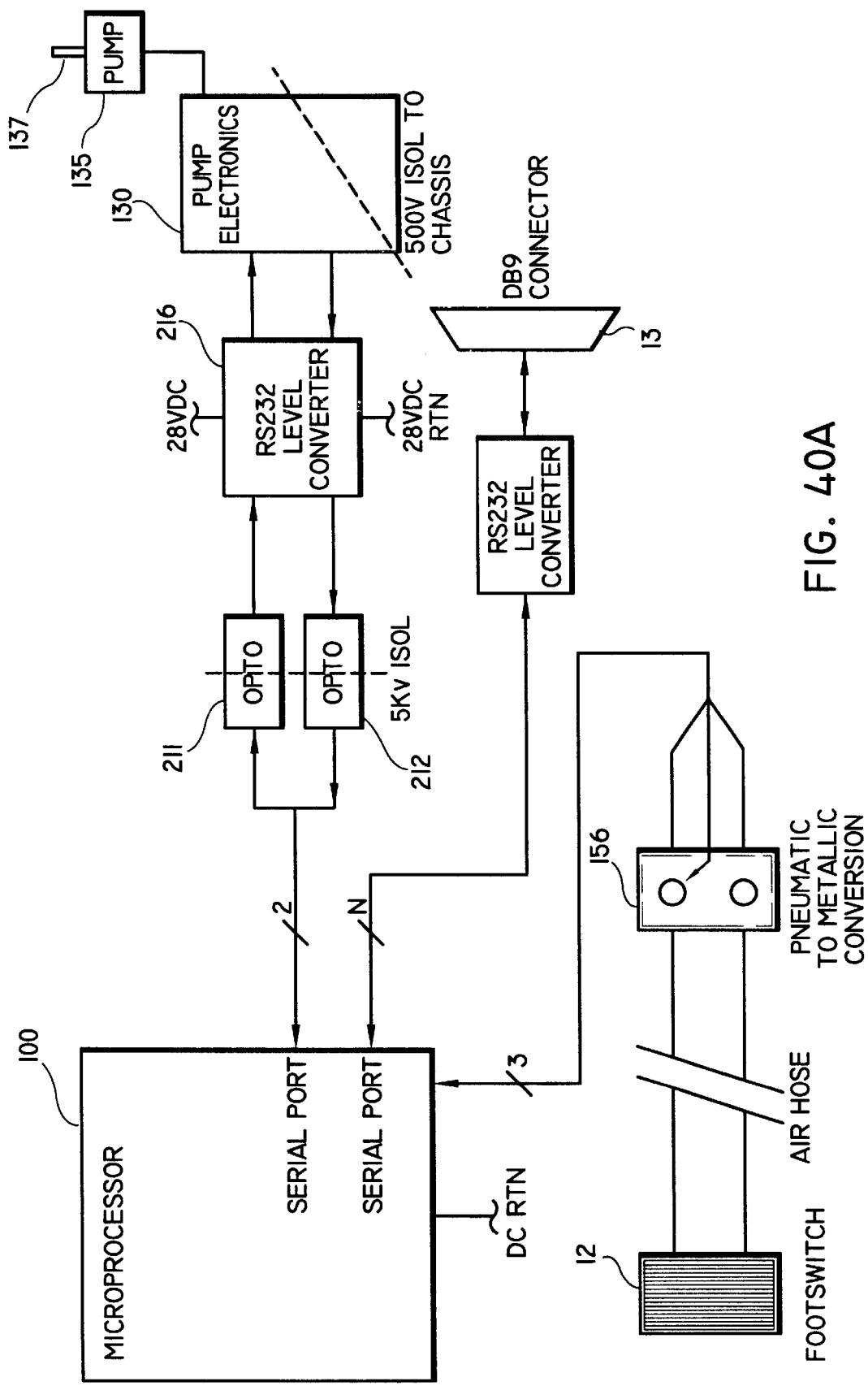
Figure 40B:
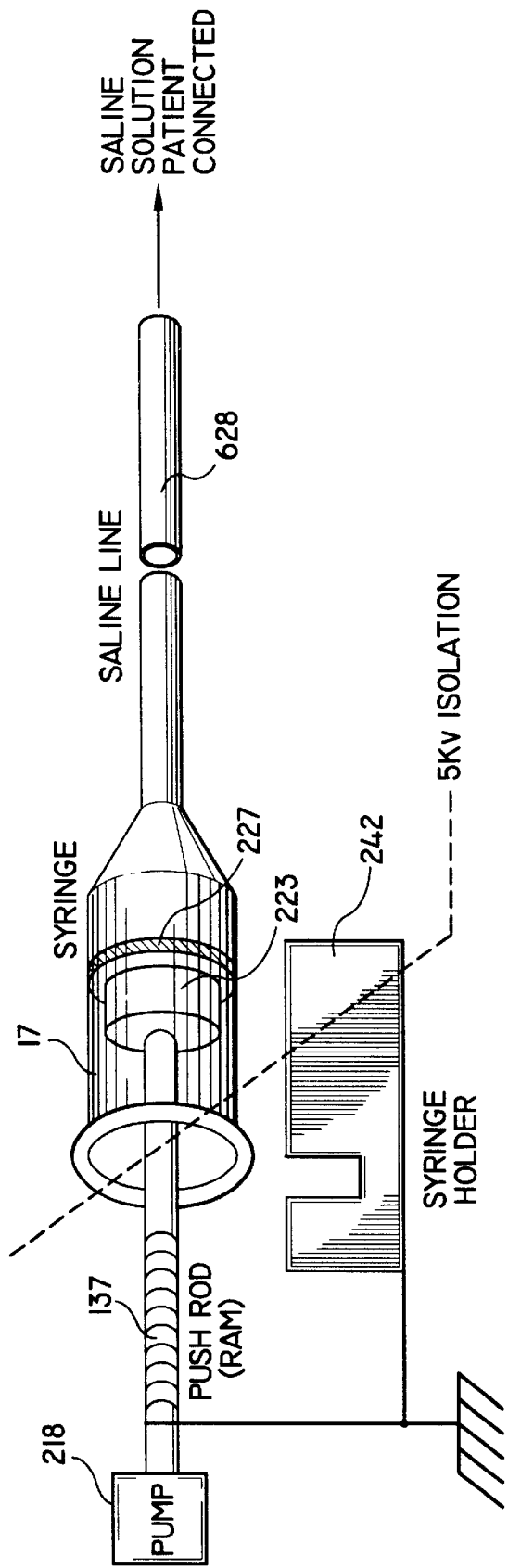
Figure 41:
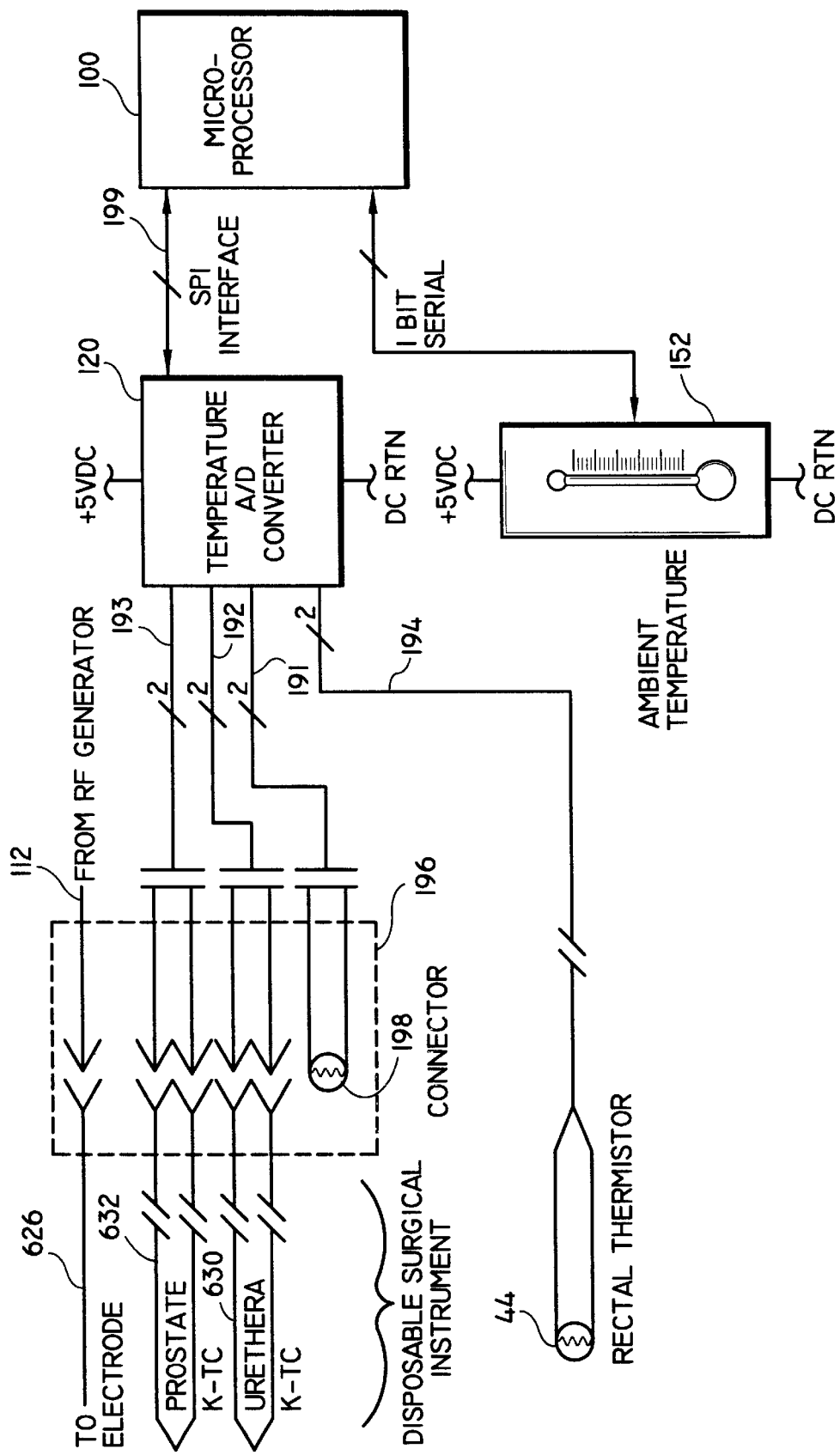

FIGS. 39–41 show exemplary controller 10 electronics in more detail. Referring to FIG. 39, RF generator 110 is of the pulse width modulation (PWM) type and simulates a sinusoidal RF output with alternating voltage pulses at a 500 KHz rate. Of course, other frequencies are possible. Microprocessor 100 controls the RF output state by providing a RF ON or RF OFF command to an opto-coupler 162 (the latter being used to isolate the microprocessor from the RF generator voltages). The command is forwarded to a D/A converter 164 which produces an output voltage in range of 0–5V DC to correspondingly control RF output power to 0–50 W. The analog voltage output from D/A converter 164 is either 0V or 5V to correspondingly produce RF power output of 0 watts (RF OFF) or 50 watts (RF ON). In other embodiments, a variable RF output power may be provided.

The above-mentioned P, V, $I_1$ and $I_2$ signals representing measured output l power, voltage, forward current and return current, respectively, are periodically forwarded as voltage pulses on respective coaxial transmission lines 172–175 to A/D converter 115. The corresponding digitized values are digitized and applied via a parallel interface to microprocessor 100. Suitable isolation (as indicated by dotted lines 178) is provided between the transmission line voltages and the RF output voltage applied to the patient.

A reset timer circuit 166 responds to a command from microprocessor 100 by an resetting an internal clock within RF generator 110. The internal clock is a 500 KHz, two phase clock which controls the output voltage waveform.

With reference to FIG. 40A, microprocessor 100 initiates saline solution flow to the patient by forwarding a command to opto-isolator 211, which in turn sends a corresponding isolated command signal to pump electronics 130 through level converter 216. Pump 135 is then controlled to drive a ram 137 at a constant rate, for example, 2 cc per minute. The constant flow rate condition occurs either when the user activates the purge switch 14c on the front panel, when the footswitch is first depressed, or, whenever RF current is caused to flow. Ram 137 is shown within syringe 17 in FIG. 40B. A second command from processor 100, initiated by user activation of the "pump retract" switch 14a, causes ram 137 to retract in the reverse direction to facilitate installing or removing the syringe. Once a new syringe is installed, the user typically depresses the "advance pump" button 14b on the controller front panel. This results in a command from microprocessor 100 to the pump electronics to cause ram 137 to move forward to a detent position ready for purge. The detent position corresponds to the pushing member 223 of ram 137 contacting a plug 227 within syringe 17 with sufficient force. (Prior to installation of syringe 17 into the hatch door compartment of controller 10, the syringe is filled and plug 227 is placed near the open end of the syringe). Feedback signals indicative of the actual position of ram 137 are fed back by pump electronics 130 to microprocessor 100 via level converter 216 and opto-isolator 212. From these feedback signals, microprocessor 100 determines a corresponding saline volume within syringe 17.

A pneumatic to metallic converter 156 is coupled to footswitch 12 via an air hose and provides signals to processor 100 indicative of the footswitch depression. When footswitch 12 is depressed, the software running on processor 100 starts a timer and initiates saline flow. A predetermined time thereafter (e.g. 30 seconds) it will start the RF current flow and continue solution flow until the threshold therapy treatment time corresponding to the selected treatment volume is reached or a safety temperature limit is reached, whichever is first. For example, the safety temperature limits may be 45° C. for the urethra, 104° C. for the prostate, and 42° C. for the rectum. If the foot switch is released, the solution flow will be stopped after a predetermined timeout duration, e.g., a two second delay, and the RF current flow will be stopped. A message indicative of the footswitch being released will be displayed on LCD display 16. If the footswitch is depressed before the timeout duration is complete, then the solution flow will continue without interruption at the prescribed rate (e.g., 2 cc/minute).

Referring to FIG. 41, temperature measuring circuit 120 digitizes analog temperature data on each copper wire pair 192, 193 and 194. Copper wire pairs 192 and 193 connect within connector 196 to the prostate and urethra thermocouple wire pairs 630 and 632, respectively. Copper wire pair 194 connects to the rectal thermistor 44. A thermistor 198 is used to measure the temperature of connector 196 in order to calibrate the thermocouple wire to the copper wire. The digitized temperature data is forwarded to processor 100 on serial port interface (SPI) 199. Processor 100 uses the temperature measured by thermistor 198 as a reference to calculate the prostate and urethra temperatures. Processor 100 also receives ambient temperature data from thermometer 152. The treatment electrode wire 626 also connects to the RF generator wire 112 within connector 196.

With reference now to FIGS. 42A–42I, a software flow diagram illustrating software running on processor 100 is presented. When the user turns the power on (step 220) a self test is performed and a corresponding message displayed on the LCD display (steps 222–226). If the self-test fails in step 228, a test fault description is display (step 230) and the user mode is suspended. Otherwise, a "self-test complete, checking instruments" message is displayed and the controller enables the pump retract button (steps 235–240). When the retract button is depressed, the pump is retracted upon command of processor 100 in steps 245–255 (unless it is already in the retracted position). With the pump retracted, the user can then unload and load the disposable syringe 17. Once the pump advance and purge buttons are enabled in step 260, the pump will be advanced to the detent position upon user depression of the pump advance button (step 270).

Next, in step 275, proper connection of the patient cable 642 is checked by means of the processor reading temperature or fault data from the temperature measuring circuit 120 (step 275). A message indicative of the cable connection is then displayed either in step 277 or 280. The software then checks for the proper connection of the disposable handle/electrode assembly 600 connected to the patient cable (step 285) and displays a corresponding message in either step 280 or 290. The it presence of the ground plate 22 (RF return) and rectal cable are then checked and corresponding messages displayed (steps 295–310).

As mentioned above, depression of the purge button 14c on the front panel, prior to insertion of the treatment catheter within the patient, causes saline to flow for the purpose of removing air from the system. The software design is such that the purge operation is a mandatory pre-operative operation. The software determines whether the purge button 14c has been pressed in step 315, and if so, solution flow is enabled and a "purge" LED is lit to verify the same to the user (steps 325–330). The software commands solution flow to continue and the purge LED is lit until the purge button is released (steps 335–345). Following the purge, the above-discussed treatment volume buttons are enabled in step 350.

Figure 42A:
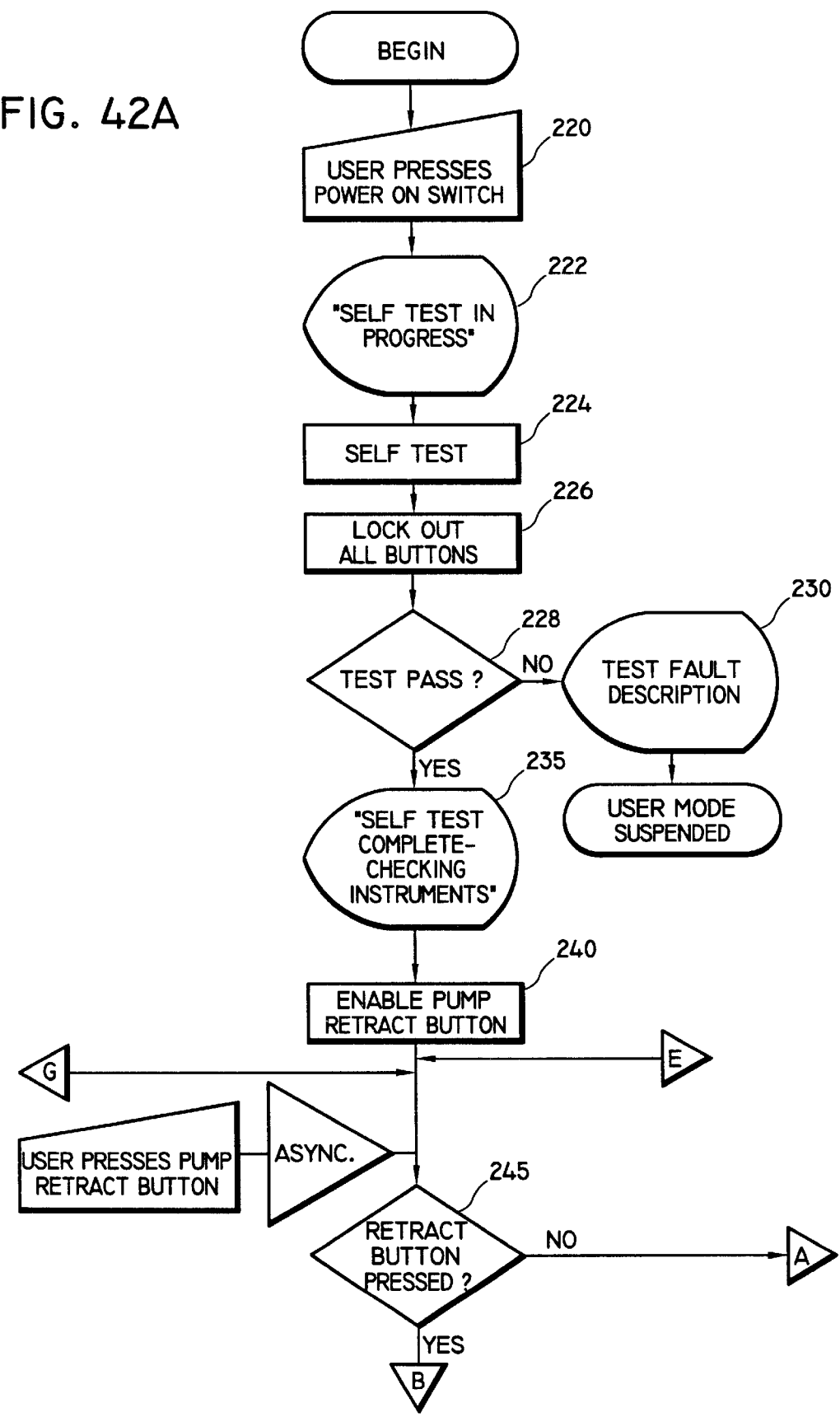
FIGS. 42A–42I are software flow diagrams representing software running on the processor within the controller.
Figure 42B:
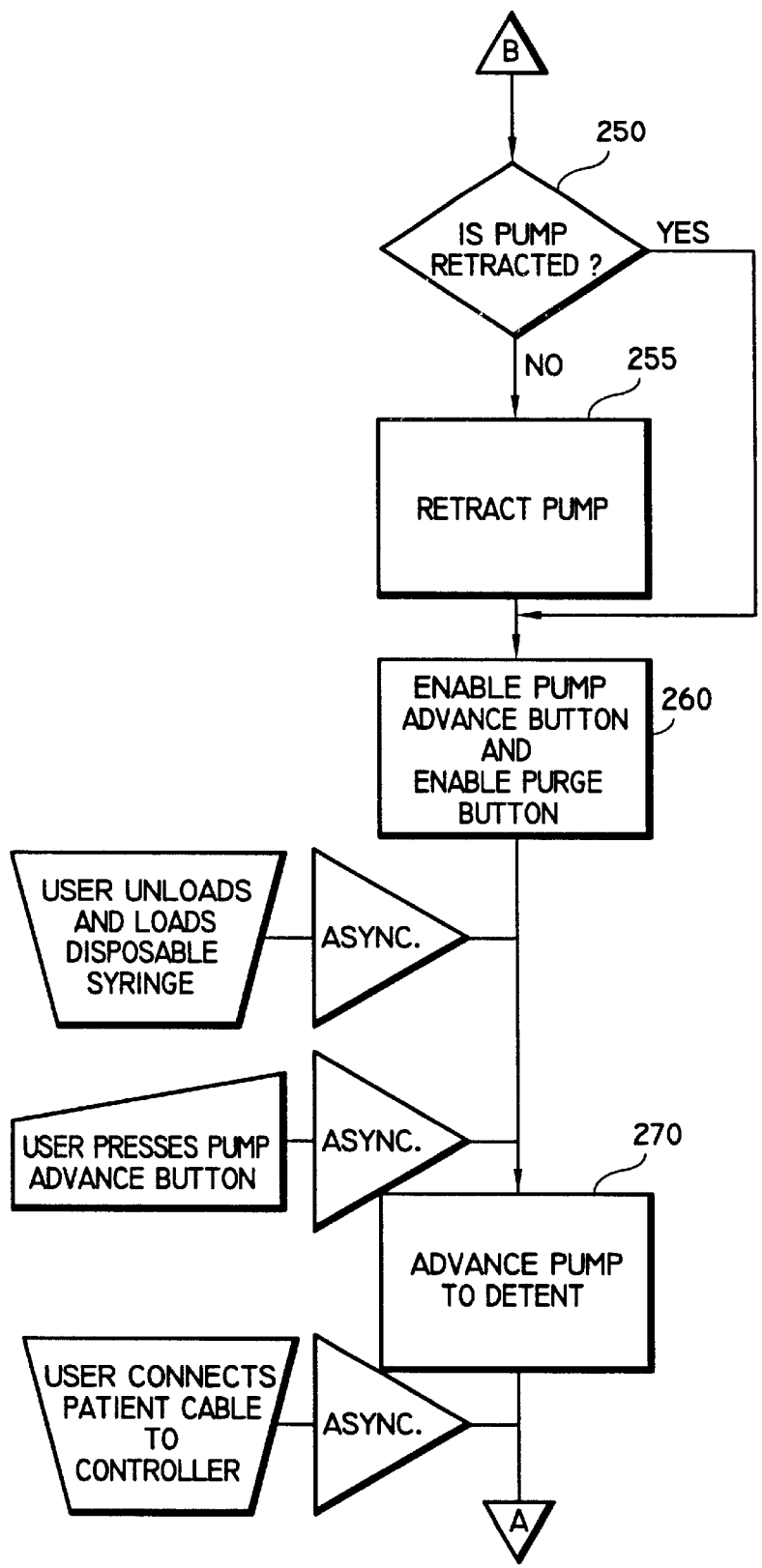
Figure 42C:
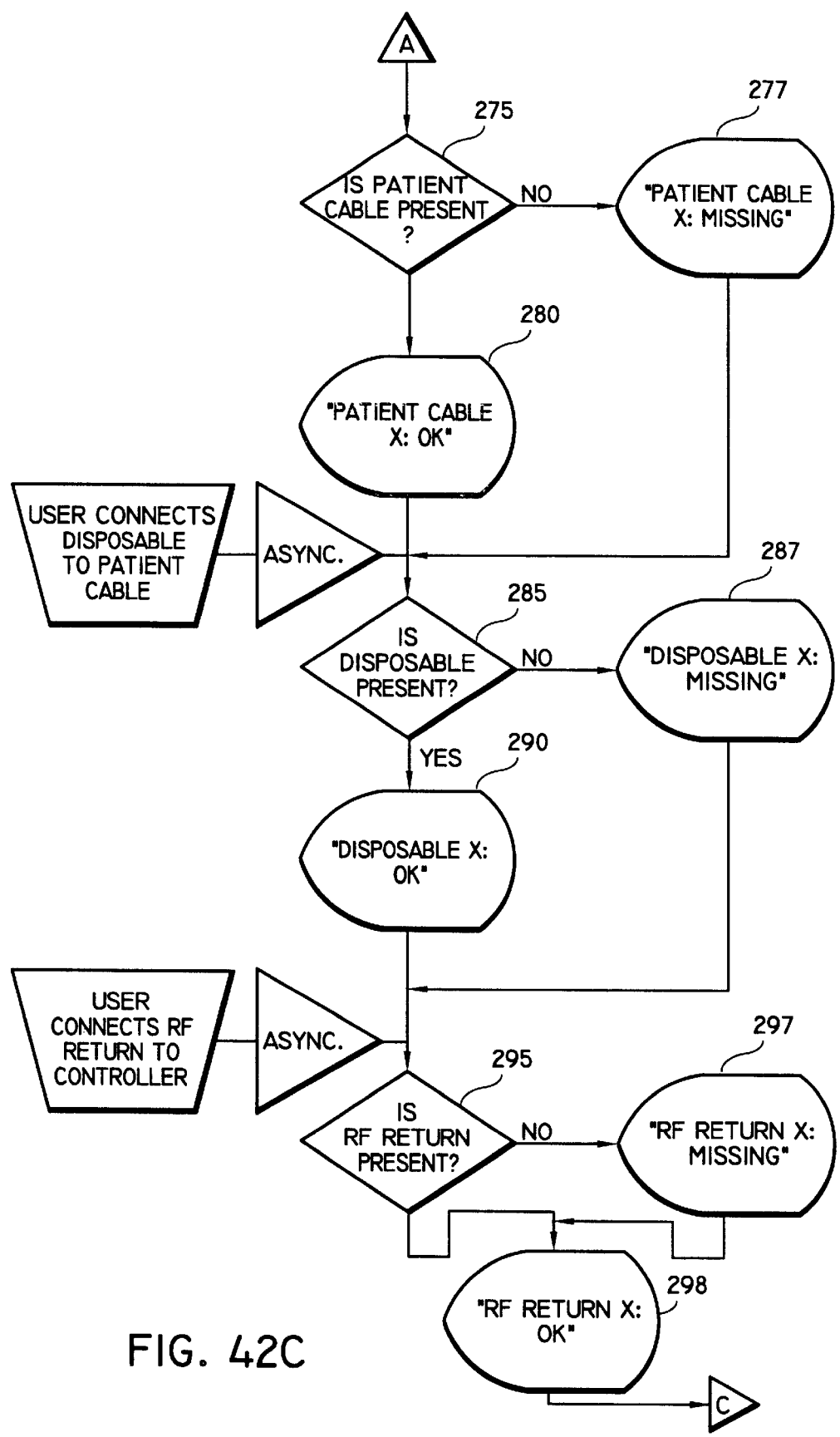
Figure 42D:
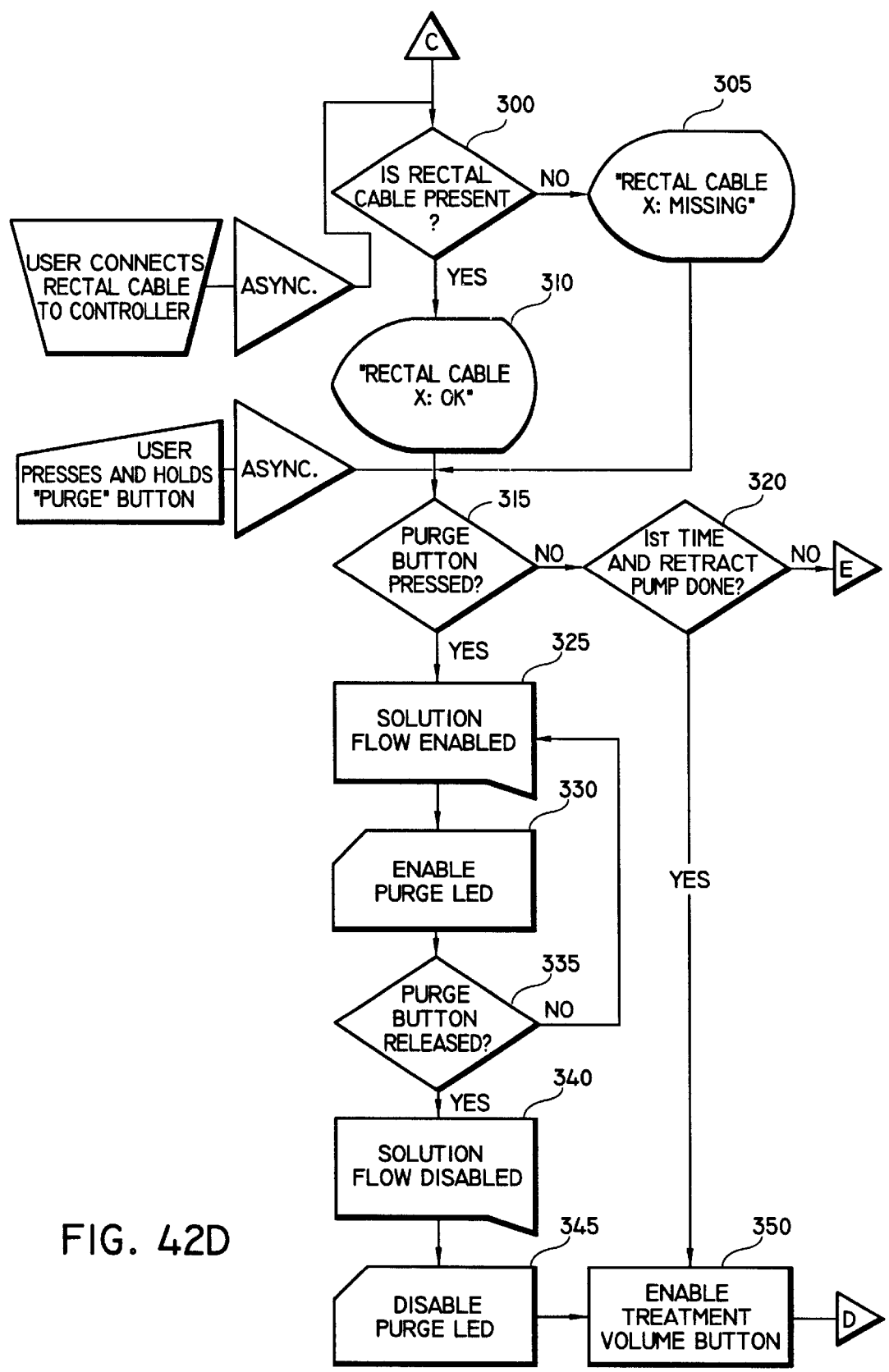
Figure 42E:
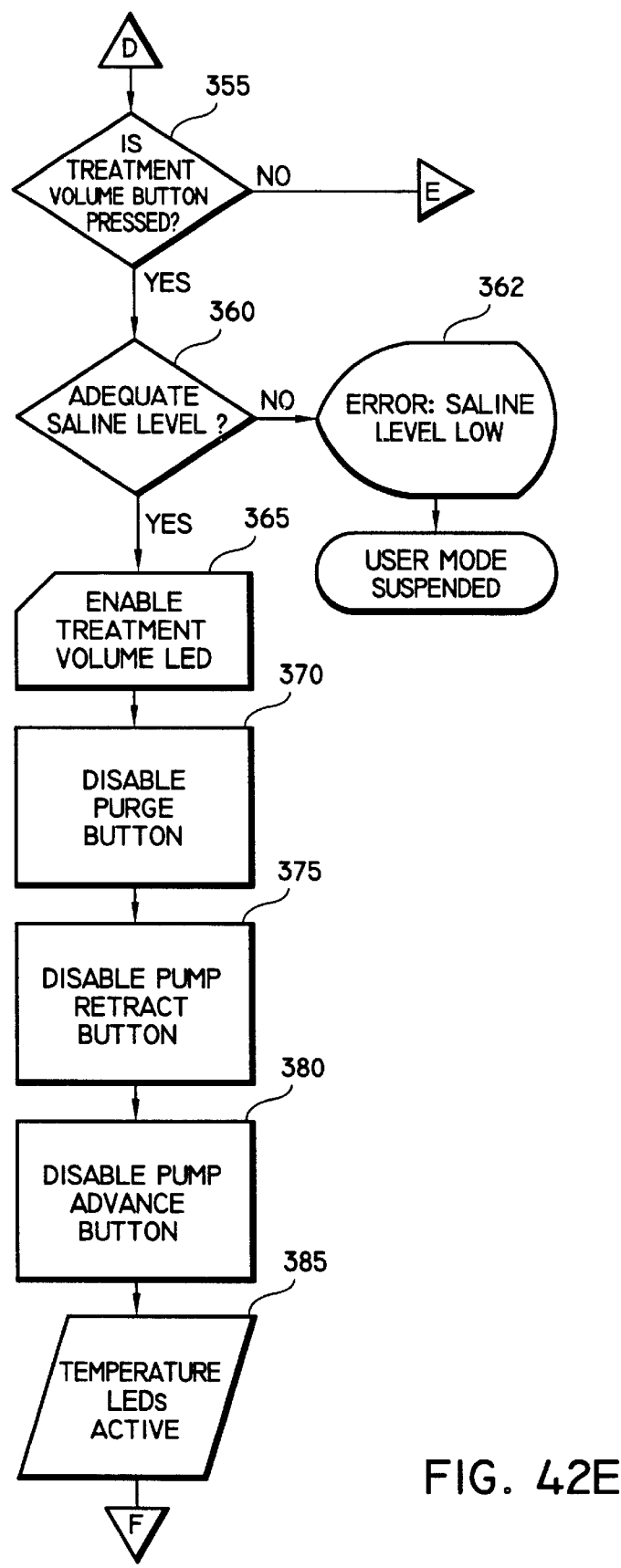
Figure 42F:
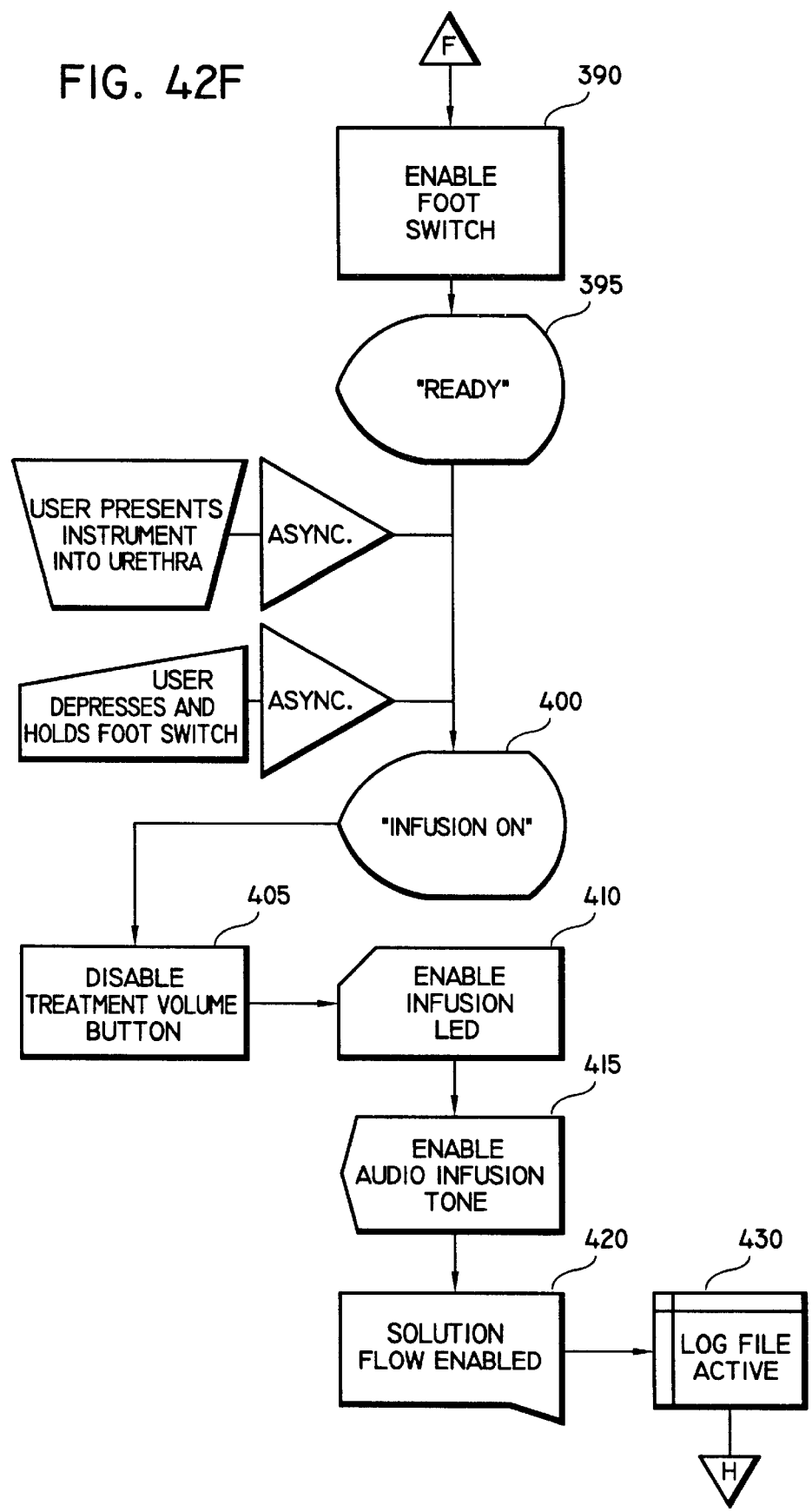
Figure 42G:
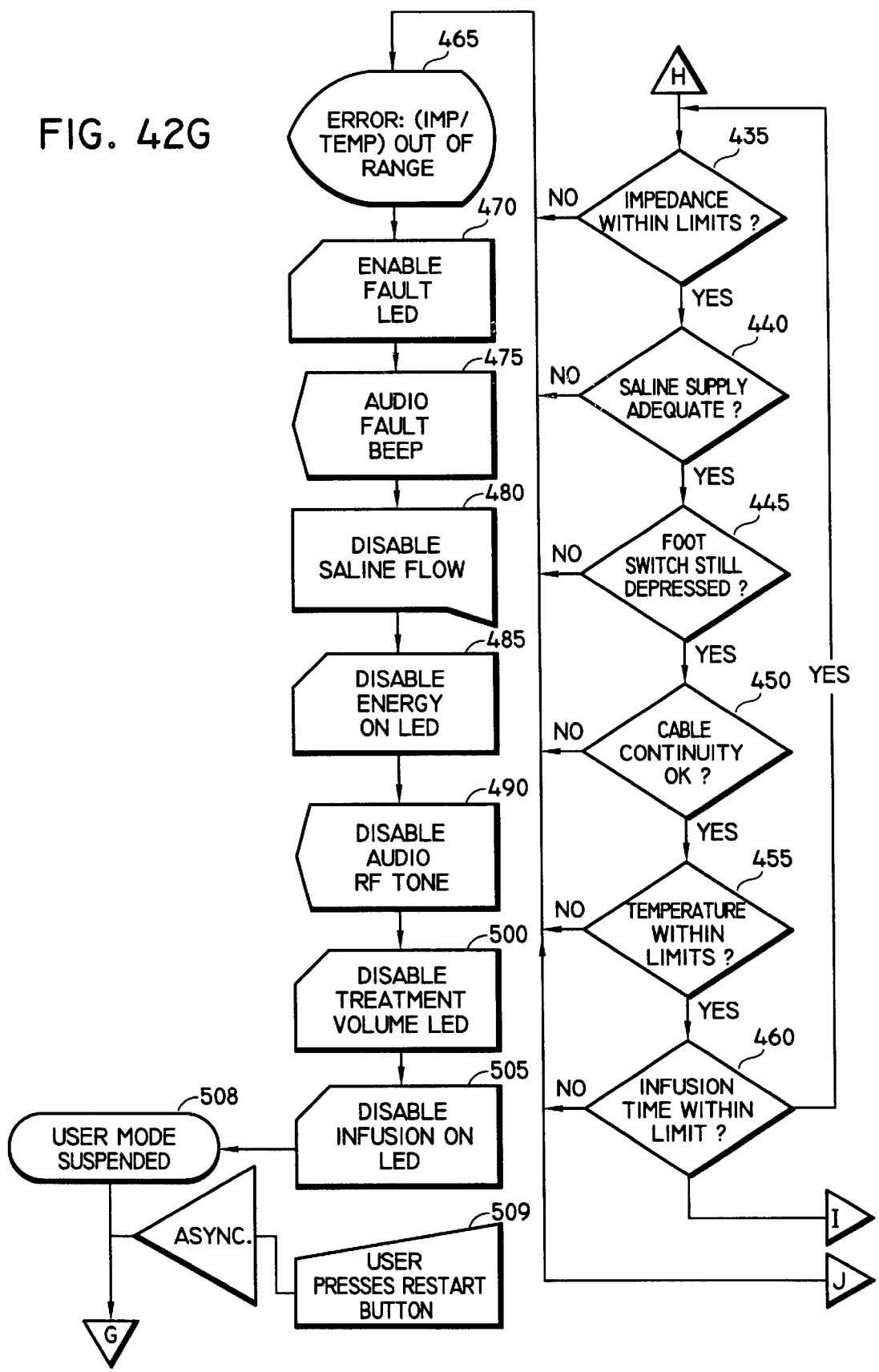
Figure 42H:
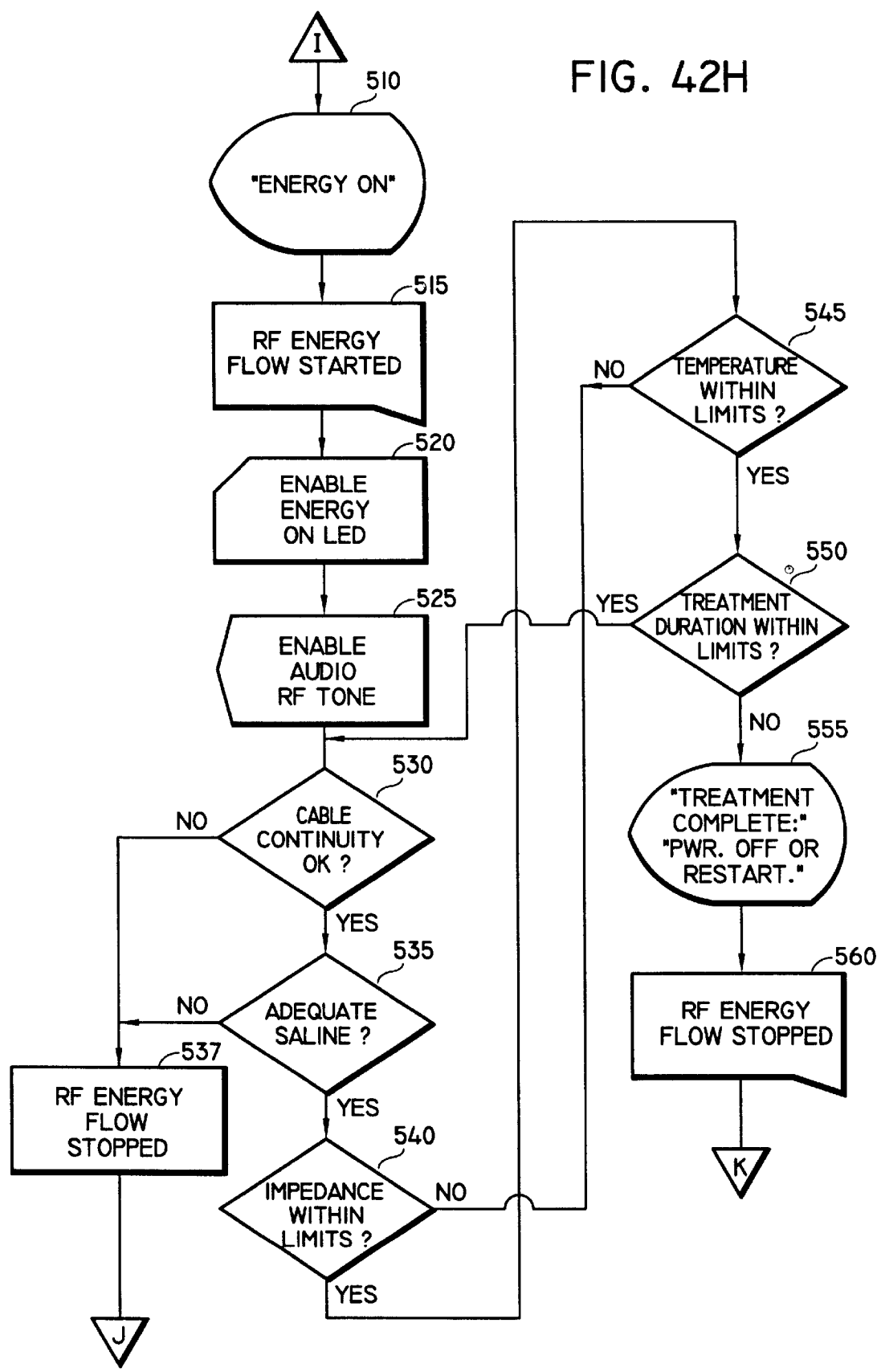
Figure 42I:
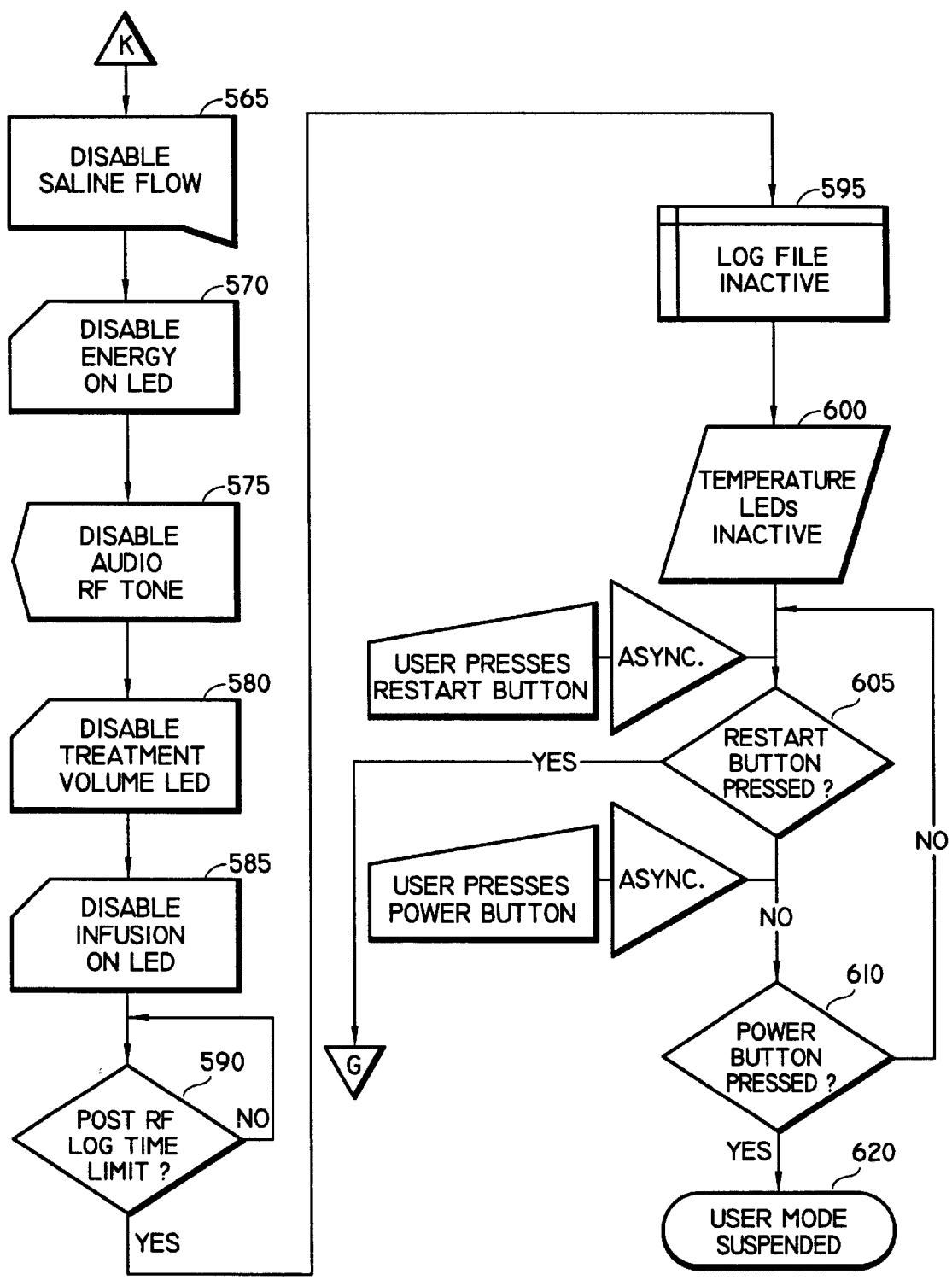

If in step 315 the purge button was not pressed, it is then determined in step 320 whether a first thermal treatment has already been performed and the pump has been retracted. If so, the flow continues to step 350. Otherwise, the software flow returns to step 245 (FIG. 42A). At this point, if one of the treatment volume buttons have been pressed in step 355 then the next step is to determine whether the saline level is adequate in step 360. (If no treatment volume button is pressed, the, flow returns to step 245 of FIG. 42A). The saline level is checked by means of feedback signals being sent from the pump electronics 130 to processor 100 indicative of the ram position, where processor 100 compares the ram position to a predetermined threshold position corresponding to an adequate saline level. If the saline level is inadequate, an error message is displayed in step 362 and the user mode is suspended. The operator would then have to fill the saline syringe and restart the procedure by activating a "restart" switch on the front panel.

If the saline level is adequate in step 360, a treatment volume LED is lit corresponding to the treatment volume selected (step 365). The purge, pump retract and pump advance buttons are then disabled in steps 370–380 whereby user depression of any of these will not disturb the saline flow. The temperature LEDs are then activated, foot switch 12 enabled and a "ready" message displayed (steps 385–395). At this juncture, the user presents the instrument into the urethra (if not already inserted). When the user depresses and holds the foot switch, the treatment commences whereupon a "infusion on" message is displayed (step 400). The treatment volume buttons are disabled in step 405 to prevent the user from changing the treatment volume at this point. An infusion LED is then lit, an audible infusion tone sounded and solution flow enabled (steps 410–420).

Next, processor 100 activates the log file in memory 105 (step 430) and begins a series of measurements and checks prior to initiating the delivery of RF power. In step 435, processor 100 computes the impedance between the electrodes based on the measured current and voltage values supplied by the RF generator. If the impedance is within limits, the processor then determines: if the saline supply is adequate; if the foot switch is still depressed; if the patient cable continuity is satisfactory; and if the measured temperature in the prostate and urethra are within limits (steps 440–455). If any of the determinations in steps 435–455 are unsatisfactory, an error message is displayed corresponding to the fault condition, a fault LED is lit and an audio fault tone sounded (steps 465–475). The occurrence of the fault causes saline flow to be disabled, LEDs to be deactivated, an audio RF tone to be disabled and the user mode suspended (steps 480–508). Once the fault condition is remedied, the user may restart the procedure by depressing the restart button (step 509) causing the software flow to return to step 245 (FIG. 42A).

Following the temperature checks of step 455, if the temperatures are within limits the software then ascertains whether a predetermined infusion time is within limit (step 460). If so, the prostate region has not been yet been fully pre-infused and the flow returns to step 435. If not, the pre-infusion period is complete and the RF energy is turned on. A corresponding text message is displayed, an LED is lit and an audio tone sounded indicating that RF is on (steps 510–525). While RF is being delivered, the software again performs checks for cable continuity and saline level (steps 530–535). RF flow is stopped in step 537 if a fault occurs, the flow then returning to step 465. Otherwise, the software checks whether the measured impedance, temperatures and treatment duration are within limits (steps 540–550). If either is out of limits, RF energy is stopped and a "treatment complete" message is displayed (steps 555–560). Otherwise, the treatment continues as the software flow returns to step 530.

Once the RF output is terminated, saline flow is disabled, as are the various LEDs and RF audio tone (steps 565–585). The log file is then deactivated following a short post RF log time interval (steps 590–595). As mentioned above, as the various parameters such as impedance, temperature and so on are measured or read by the processor during the procedure, the data is written into the log file at periodic intervals. Finally, the temperature LEDs are deactivated and the user mode suspended, unless the restart button is depressed to begin another procedure.

While the above description contains many specifics, these specifics should not be construed as limitations on the scope of the disclosure, but merely as exemplifications of preferred embodiments thereof. For example, the above-described controller may be modified to deliver RF current between a pair of bipolar electrodes as an alternative to the monopolar operation described. Further, the RF energy could be delivered to the target body region over a wide range of RF frequencies, including the microwave band. Those skilled in the art will envision many other possible variations that are within the scope and spirit of the disclosure as defined by the claims appended hereto.

What is claimed is:

1. An apparatus for use in conjunction with a radio frequency (RF) ablation electrode insertable into a patient to ablate body tissue by delivering RF current therethrough, said apparatus comprising:

an RF generator for outputting RF current sufficient to ablate body tissue;

processing circuitry, coupled to said RF generator, for controlling said RF generator;

input means, coupled to said processing circuitry, for enabling a user to input a representation of a numerical value of a treatment volume corresponding to a target volume of body tissue to be ablated; and a memory for storing a treatment time of RF power delivery corresponding to said treatment volume inputted, wherein said processing circuitry operates to command said RF generator to cease delivery of RF current when said treatment time is reached.

2. The apparatus of claim 1, further including temperature measuring circuitry coupled to a temperature sensor in a specific body region for measuring temperature in that body region; and wherein:

said memory stores at least one safety temperature limit for said specific body region; and, said processing circuitry being operative to command said RF generator to cease delivery of RF current if said safety temperature limit is reached.

3. The apparatus of claim 2, wherein said specific body region in which said temperature sensor is disposed comprises the prostate region, and further wherein said temperature measuring circuitry is coupled to at least one additional sensor disposed in a different body region, said RF generator being caused to cease delivery of RF current if the temperature in the different body region exceeds an associated threshold.

4. The apparatus of claim 1, further comprising a second electrode, wherein said radio frequency (RF) ablation electrode is part of the apparatus, and wherein said second electrode and said radio frequency (RF) ablation electrode are in contact with the patient.

5. The apparatus of claim 4, wherein said second electrode comprises a ground plate adapted to be placed in abutting relation to the patient's skin, the apparatus thereby operative to ablate body tissue in a monopolar mode.

6. The apparatus of claim 4, further including impedance measuring circuitry for measuring impedance been said ablation and second electrodes, and means for terminating the delivery of RF current if the measured impedance exceeds a threshold impedance value.

7. The apparatus of claim 1, wherein said input means comprises a plurality of user-activated switches on said apparatus, each corresponding to a specific treatment volume or range.

8. The apparatus of claim 1, wherein said processing circuitry comprises a microprocessor coupled to said memory.

9. The apparatus of claim 1, wherein said RF generator outputs sufficient RF current to ablate prostate tissue.

10. The apparatus of claim 1 further including an infusion pump for pumping a fluid into a body region encompassing said body tissue to be ablated, said infusion pump being controlled by said processing circuitry to pump said fluid at a controlled rate.

11. The apparatus of claim 10, further including means for mounting a syringe containing said fluid, said fluid being pumped out of said syringe through a fluid line connected to said apparatus, by means of a ram driven by said infusion pump.

12. The apparatus of claim 10, wherein said fluid comprises hypertonic saline solution.

13. The apparatus of claim 1, wherein said processing circuitry is operable to maintain a log file in a memory including date and time of treatment, treatment volume selected and measured temperature data in periodic intervals during the treatment.

14. The apparatus of claim 13, wherein said processing circuitry is operable to store in said log file, at periodic intervals during the course of each treatment, measured prostate, urethral and rectal temperatures, impedance between said ablation and second electrodes, and forward and return RF current from said RF generator.

15. The apparatus of claim 1, wherein said input means comprises a plurality of user-activated switches on said apparatus, each corresponding to a specific treatment volume, including first, second and third switches corresponding to treatment volumes of less than 4 cm³, 4 cm³–8 cm³, and greater than 8 cm³, respectively.

16. The apparatus of claim 1, further comprising means for determining the volume of tissue to be ablated.

17. The apparatus of claim 16, wherein said means for determining comprises:
   an ultrasound instrument; and
   a rectal probe attached to said ultrasound instrument.

18. An apparatus for use in conjunction with a transurethral radio frequency (RF) ablation electrode insertable into a patient's prostate region to ablate prostate tissue by delivering RF current therethrough, said apparatus comprising:
   an RF generator for outputting RF current sufficient to ablate prostate tissue;
   processing circuitry for controlling delivery of RF current by said RF generator;
   temperature measuring circuitry coupled to a temperature sensor in a specific body region for measuring temperature in that body region;
   input means, coupled to said processing circuitry, for enabling a user to input a treatment volume corresponding to a target volume of body tissue to be ablated;
   wherein said processing circuitry operates to compare the measured temperature with a threshold value corresponding to the treatment volume selected, and further operates to command said RF generator to cease delivery of RF current if said measured temperature exceeds said threshold value; and
   an infusion pump for pumping a fluid into the prostate region, said infusion pump being responsive to commands generated by said processing circuitry to pump said fluid at a controlled rate.

19. The apparatus of claim 18 wherein said fluid comprises hypertonic saline solution.

20. The apparatus of claim 18, further including means for mounting a syringe containing said fluid, said fluid being pumped out of said syringe through a fluid line connected to said apparatus, by means of a ram driven by said infusion pump.

21. The apparatus of claim 18 wherein said infusion pump is operative, under control of said processing circuitry, to pump said fluid at a controlled rate both immediately prior to delivery of RF current and during delivery of RF current.

22. An apparatus for use in conjunction with a transurethral radio frequency (RF) ablation electrode insertable into a patient's prostate region to ablate prostate tissue by delivering RF current therethrough, said apparatus comprising:
   an RF generator for outputting RF current in a monopolar mode sufficient to ablate prostate tissue;
   processing circuitry for controlling delivery of RF current by said RF generator;
   an infusion pump for pumping hypertonic saline solution into the prostate region, said infusion pump being responsive to commands generated by said processing circuitry to pump said solution at a controlled rate both immediately prior to delivery of RF current and during delivery of RF current;
   means for mounting a syringe containing said solution, said solution being pumped out of said syringe through a fluid line connected to said apparatus, by means of a ram driven by said infusion pump;
   input means, coupled to said processing circuitry, for enabling a user to input a treatment volume corresponding to a target volume of body tissue to be ablated;
   a memory for storing a treatment time of RF power delivery corresponding to said treatment volume inputted; and
   said processing circuitry being operative to command said RF generator to cease delivery of RF current when said treatment time is reached.

23. The apparatus of claim 12, further including temperature measuring circuitry coupled to a temperature sensor in a specific body region for measuring temperature in that body region; and wherein:
   said memory stores at least one safety temperature limit for said specific body region; and,
   said processing circuitry being operative to command said RF generator to cease delivery of RF current if said safety temperature limit is reached.

24. An apparatus for use in conjunction with a radio frequency (RF) ablation electrode insertable into a patient to ablate body tissue by delivering RF current therethrough, said apparatus comprising:
   an RF generator for outputting RF current sufficient to ablate body tissue;
   temperature measuring circuitry coupled to a temperature sensor in a specific body region for measuring temperature in that body region;
   processing circuitry, coupled to said RF generator, for controlling said RF generator; and
   input means, coupled to said processing circuitry, for enabling a user to input a treatment volume corresponding to a target volume of body tissue to be ablated;
   wherein said processing circuitry operates to compare the measured temperature with a threshold value corresponding to the treatment volume selected, and further operates to command said RF generator to cease delivery of RF current if said measured temperature exceeds said threshold value.

25. The apparatus of claim 24, wherein said second electrode comprises a ground plate adapted to be placed in abutting relation to the patient's skin, said apparatus thereby operative to ablate body tissue in a monopolar mode.

26. The apparatus of claim 24, wherein said input means comprises a plurality of user-activated switches on said apparatus, each corresponding to a specific treatment volume or range.

27. The apparatus of claim 24, wherein said processing circuitry comprises a microprocessor that retrieves said threshold value from a memory.

28. The apparatus of claim 24, wherein said RF generator outputs sufficient RF current to ablate prostate tissue.

29. The apparatus of claim 28, wherein said specific body region in which said temperature sensor is disposed comprises the prostate region, and further wherein said temperature measuring circuitry is coupled to at least one additional sensor disposed in a different body region, said RF generator being caused to cease delivery of RF current if the temperature in the different body region exceeds a threshold.

30. The apparatus of claim 24 further including an infusion pump for pumping a solution into a body region encompassing said body tissue to be ablated, said infusion pump being controlled by said processing circuitry to pump said fluid at a controlled rate.

31. The apparatus of claim 30, further including means for mounting a syringe containing said fluid, said fluid being pumped out of said syringe through a fluid line connected to said apparatus, by means of a ram driven by said infusion pump.

* * * * *